(12) United States Patent
Jaouen et al.

(10) Patent No.: US 9,758,541 B2
(45) Date of Patent: Sep. 12, 2017

(54) METALLOCENE DERIVATIVES WITH ANTICANCER ACTIVITY

(71) Applicant: Paris Sciences et Lettres—Quartier Latin, Paris (FR)

(72) Inventors: Gerard Jaouen, Cachan (FR); Pascal Pigeon, Paris (FR); Siden Top, Lisses (FR)

(73) Assignee: PARIS SCIENCES ET LETTRES—QUARTIER LATIN (FR)

( * ) Notice: Subject to any disclaimer, the term of this patent is extended or adjusted under 35 U.S.C. 154(b) by 0 days.

(21) Appl. No.: 15/032,877

(22) PCT Filed: Oct. 30, 2014

(86) PCT No.: PCT/EP2014/073308
§ 371 (c)(1),
(2) Date: Apr. 28, 2016

(87) PCT Pub. No.: WO2015/063201
PCT Pub. Date: May 7, 2015

(65) Prior Publication Data
US 2017/0166600 A1 Jun. 15, 2017

(30) Foreign Application Priority Data

Oct. 30, 2013 (EP) .................................. 13306480

(51) Int. Cl.
*C07F 17/02* (2006.01)
*A61K 31/295* (2006.01)
*A61K 31/555* (2006.01)

(52) U.S. Cl.
CPC ............ *C07F 17/02* (2013.01); *A61K 31/295* (2013.01); *A61K 31/555* (2013.01)

(58) Field of Classification Search
None
See application file for complete search history.

(56) References Cited

FOREIGN PATENT DOCUMENTS

| WO | 2006/005856 A1 | 1/2006 |
| WO | 2006005856 | * 1/2006 |
| WO | 2010/000793 A1 | 1/2010 |
| WO | 2010000793 | * 1/2010 |

OTHER PUBLICATIONS

Hillard et al., Journal of Organometallic Chemistry 692 (2007) 1315-1326.*
Lippert, Bernhard, "Cisplatin: Chemistry and Biochemistry of a Leading Anticancer Drug", John Wiley and Sons, New York, 1999, pp. 54-57.
Reedijk, Eur. J. Inorg. Chem., 2009, 1303-1312.
International Search Report issued from corresponding PCT/EP2014/073308, dated Feb. 12, 2015.
Hillard et al: "Organometallic diphenols: The importance of the organometallic moiety on the expression of a cytotoxic effect on breast cancer cells", Journal of Organometallic Chemistry. Elsevier-Sequoia S.A. Lausanne. CH. vol. 692. No. 6. Feb. 12, 2007 (Feb. 12, 2007). pp. 1315-1326. XP005880405.
Allardyce, C.S. et al., [Ru(n6-p-cymene)C12(pta)] (pta=1,3,5-triaza-7-phosphatricyclo[3.3.1.1]decane): a water soluble compound that exhibits pH dependent DNA binding providing selectivity for diseased cells, Chem. Commun., 2001, 1396-1397.
Ferreira A. et al., Synthesis and Characterization of New Organometallic Benzo[b]thiophene Derivatives with Potential Antitumor Properties, Organometallics, 2009, 28, 18, 5412-5423.
Hillard et al., Ferrocene-Mediated Proton-Coupled Electron Transfer in a Series of Ferrocifen-Type Breast-Cancer Drug Candidates, Angewandte Chemie, International Edition, 2006, 45(2), 285-290.
Hillard et al., The influence of phenolic hydroxyl substitution on the electron transfer and anti-cancer properties of compounds based on the 2-ferrocenyl-1-phenyl-but-1-ene motif, Dalton Transactions, 2007, 43, 5073-5081.
Huynh N.T. et al., Treatment of 9L Gliosarcoma in Rats by Ferrociphenol-Loaded Lipid Nanocapsules Based on a Passive Targeting Strategy via the EPR Effect, Pharm. Res., 2011, 28, 3189-3198.
Jaouen G. et al., Organometallics targeted to specific biological sites: the development of new therapies, Jaouen G Ed. Wiley-VCH: Weinheim in Bioorganometallics, 2005, 65-95.
Kumar et al., Directing spatial disposition of ferrocene around homoadenine tetrads, Chemical Communications, 2008, 22, 2526-2528.
Laine A.-L. et al., The in vivo performance of ferrocenyl tamoxifen lipid nanocapsules in xenografted triple negative breast cancer, Biomaterials, 2013, 34, 28, 6949-6956.

(Continued)

*Primary Examiner* — Karl J Puttlitz
(74) *Attorney, Agent, or Firm* — Banner & Witcoff, Ltd.

(57) ABSTRACT

The present invention relates to a compound of the following formula (I) or a pharmaceutically acceptable salt or solvate thereof, a stereoisomer or a mixture of stereoisomers in any ratio, or a water-soluble derivative, as well as to methods for preparing same and to the use thereof, in particular in the treatment of cancer.

18 Claims, No Drawings

(56) References Cited

OTHER PUBLICATIONS

Metay E. et al., Synthesis and Anion-Binding Properties of Novel Redox-Active Calixarene Receptors, Eur. J. of Organic Chem., 2008, 25, 4304-4312.

Nakayama J. et al., 1, 1,2,2-Tetrakis(2-triptycyl)ethylene, Chem. Com., 1986, 12, 974-975.

Rosenberg B. et al., Platinum Compounds: A New Class of Potent Antitumour Agents, Nature, 1969, 222, 385-386.

Rosenberg B. et al., Inhibition of Cell Division in *Escherichia coli* by Electrolysis Products from a Platinum Electrode, Nature, 1965, 205, 698-699.

Siddiqi et al., Thermal Stability and Sublimation Pressures of Some Ruthenocene Compounds, Materials, 2010, 3, 1172-1185.

Top et al., Synthesis, Biochemical Properties and Molecular Modelling Studies of Organometallic Specific Estrogen Receptor Modulators (SERMs), the Ferrocifens and Hydroxyferrocifens: Evidence for an Antiproliferative Effect of Hydroxyferrocifens on both Hormone-Dependent and Hormone-Independent Breast Cancer Cell Lines, Chem. Eur. J., 2003, 9, 5223-5236.

Top et al., Facile route to ferrocifen, 1-[4-(2-dimethylaminoethoxy0]-1-(phenyl-2-ferrocenyl-but-1-ene), first organometallic analogue of tamoxifen, by the McMurry reaction, J. of Organometallic Chemistry, 1997, 541 (1-2), 355-361.

Top et al., Studies on organometallic selective estrogen receptor modulators, (SERMs) Dual activity in the hydroxyl-ferrocifen series, J. Organomet. Chem., 2001, 637, 500-506.

Vessieres, A. et al., Metal complex SERMs (selective oestrogen receptor modulators). The influence of different metal units on breast cancer cell antiproliferative effects, Dalton Trans., 2006, 4, 529-541.

Vessieres, A. et al., Modification of the Estrogenic Properties of Diphenols by the Incorporation of Ferrocene, Generation of Antiproliferative Effects in Vitro, J. Med. Chem., 2005, 48, 3937-3940.

Wang F. et al., Reactions of a Ruthenium(II) Arene Antitumor Complex with Cysteine and Methionine, Inorg. Chem., 2002, 41, 4509-4523.

Wong E. et al., Current Status of Platinum-Based Antitumor Drugs, Chem. Rev., 1999, 99, 2451-2466.

Reedijk, J., Platinum Anticancer Coordination Compounds: Study of DNA Binding Inspires New Drug Design Eur. J. Inorg. Chem., 2009, 1303-1312.

Lippert B., Cisplatin: Chemistry and Biochemistry of a Leading Anticancer Drug, John Wiley and Sons, New York, 1999.

* cited by examiner

METALLOCENE DERIVATIVES WITH ANTICANCER ACTIVITY

RELATED APPLICATION DATA

This application is a National Stage Application under 35 U.S.C. 371 of co-pending PCT application number PCT/EP2014/073308 designating the United States and filed Oct. 30, 2014; which claims the benefit of EP application number 13306480.8 and filed Oct. 30, 2013, each of which are hereby incorporated herein by reference in their entireties.

The present invention relates to metallocene derivatives useful for the treatment of cancer, as well as the processes for preparing them and their uses as a medicine, notably in the treatment of cancer.

Due to the longer life expectancy, cancer, the leading cause of mortality in France, is affecting more and more people.

However, about ⅓ of cancers still remain incurable (more than 90% of mortality within the year of diagnosis) due to the fact that they have intrinsic resistance to pro-apoptotic stimuli and that more than 85% of the cancer treatments currently available are pro-apoptotic compounds, such as DNA alkylating agents. Such incurable cancers include for example gliomas, melanomas, non-small-cell lung cancers, ovarian cancers, esophageal cancers, pancreatic cancers, head and neck cancers, prostate cancer and non-hormone-dependent breast cancer and they concern about 13.5 million of patients.

There is thus a need for new treatments inducing cell death via a non-apoptotic route to combat these currently incurable cancers.

Following Rosenberg's discovery of anticancer effects of cisplatin (Rosenberg, B. et al. *Nature* 1969, 222, 385-386; Rosenberg, B. et al. *Nature* 1965, 205, 698-699; Wong, E. et al. *Chem. Rev.* 1999, 99, 2451-2466), the use of metal-coordinated derivatives in medicine has been developed. Currently four classes of these types of coordination complex representatives are commercially available. These are as follows:

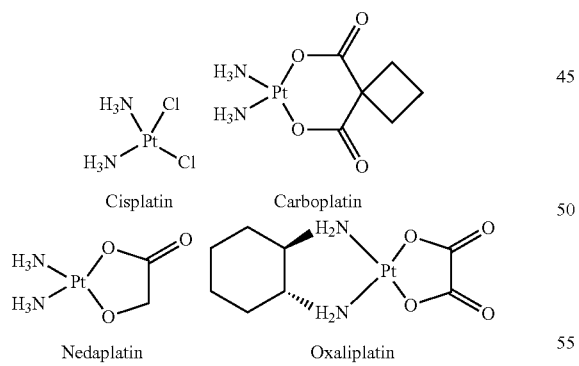

Cisplatin  Carboplatin

Nedaplatin  Oxaliplatin

Upon hydrolysis, they initially act by combining directly with DNA so as to prevent cell replication (Lippert, B. *Cisplatin: Chemistry and Biochemistry of a Leading Anticancer Drug.* John Wiley and Sons: New York, 1999). However, despite their therapeutic value, these complexes suffer from several deficiencies such as severe systemic toxicity, rapid onset of resistance, low selectivity, kidney damage and a relatively narrow therapeutic efficacy range. Moreover, they are ineffective in cancer resistant to apoptosis.

It is however possible to introduce new paradigms in the field of metallodrugs by taking advantage of the versatility of organometal chemistry which provided the opening of a new interface (Vessiéres, A. et al. *Dalton Trans.* 2006, 4, 529-541; Jaouen, G. et al. Organometallics targeted to specific biological sites: The development of new therapies. In *Bioorganometallics*, Jaouen, G., Ed. Wiley-VCH: Weinheim, 2005; pp 65-95).

Thus, ferrocene compounds which are structural analogs of chloroquine, a drug that is unfortunately resistant to new strains of malaria, showed an antimalarial activity while being able to overcome this resistance, thus resulting in ferroquine, i.e. one of these ferrocene compounds, being in clinical phase IIb at Sanofi-Aventis. Likewise, two arene complexes of ruthenium (A) and (B) have entered clinical trials as antimetastatics (Wand, F. et al. *Inorg. Chem.* 2002, 41, 4509-4523; Allardyce, C. S. et al. *Chem. Commun.* 2001, 1396-1397).

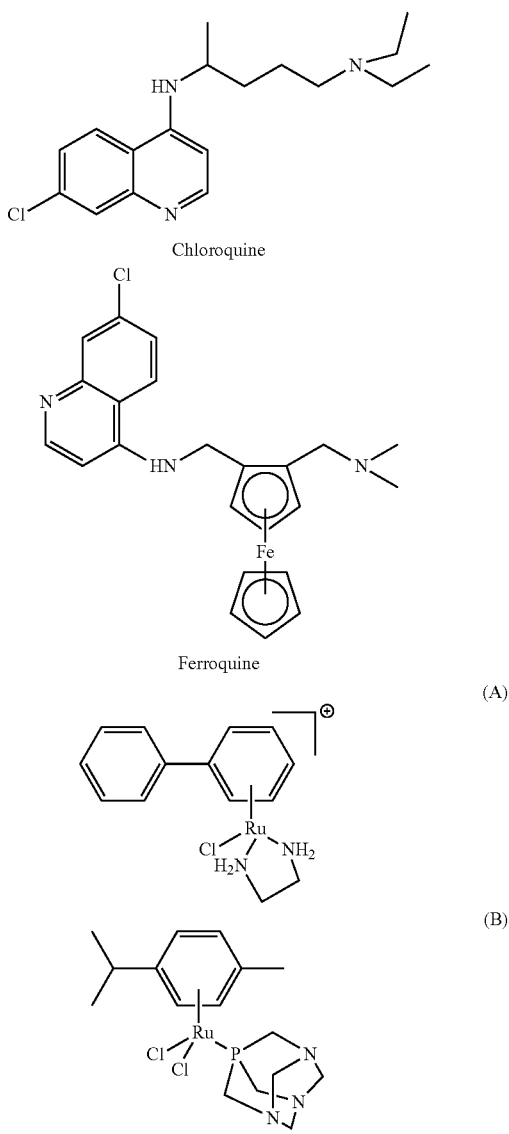

Likewise, molecules 1, 2, 3 and 4 below have been tested in vitro (Top, S. et al. *Chem. Eur. J.* 2003, 9, 5223-5236; Vessiéres, A. et al. *J. Med. Chem.* 2005, 48, 3937-3940; Top, S. et al. *J. Organomet. Chem.* 2001, 637, 500-506; Hillard et al. *J. Organomet. Chem.* 2007, 692, 1315-1326; Hillard et al. *Angewandte Chemie, International Edition* 2006, 45(2), 285-290; Hillard et al. *Dalton Transactions* 2007, 43, 5073-5081) and in vivo (Laine, A.-L. et al. *Biomaterials* 2013, 34, 28, 6949-6956; Huynh, N. T. et al. *Pharm. Res.* 2011, 28, 3189-3198).

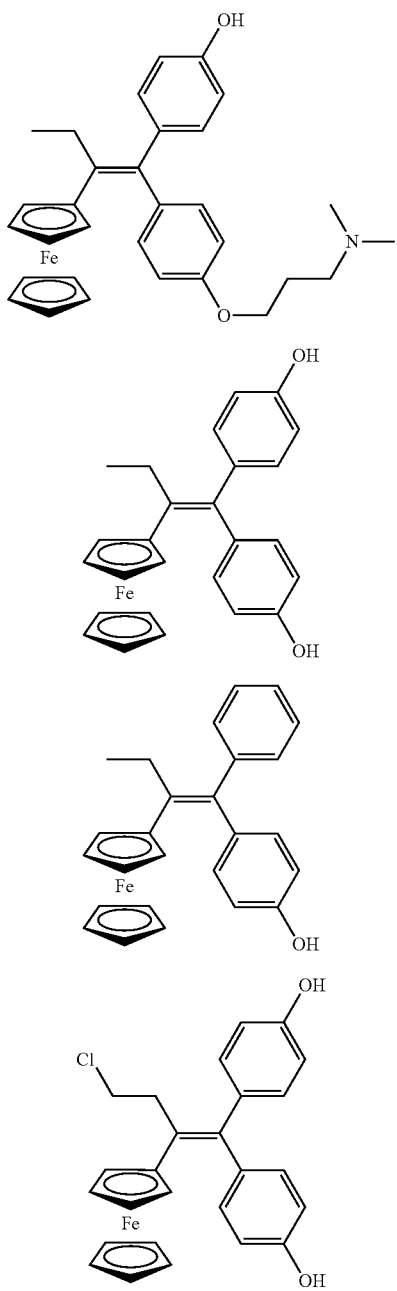

Thus, molecule 1 is partly similar in its effects to tamoxifen since it has the same type of antiestrogen activity on hormone-dependent breast tumors (ER+type) but is different from the latter in its antiproliferative behavior on non-hormone-dependent tumors (ER−).

Molecules 2 and 3 display antiproliferative activity on lines of breast cancers (MCF-7, MDA-MB-231) and prostate cancers (PC-3, DU-145).

Molecule 4 displays also antiproliferative activity on the same lines of breast cancers (MCF-7, MDA-MB-231) but its activity is lower than the one of molecule 2 (unsubstituted analog).

Unfortunately the above-mentioned open molecules 1, 2, 3 and 4, are still not optimum as such for a likely development.

Other ferrocene derivatives have thus been developed and described in WO 2010/000793. These derivatives have the following formulas:

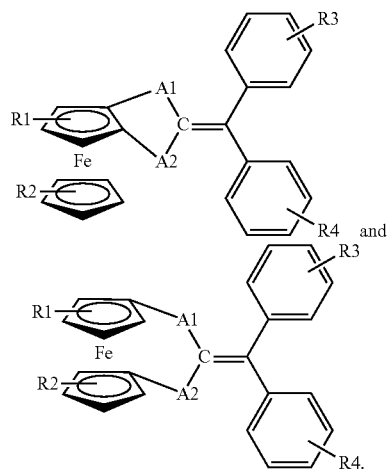

The inventors of the present invention have now surprisingly discovered a new family of metallocene derivatives, and in particular ferrocene derivatives, having an anticancer activity higher than that of molecules 1, 2, 3, or 4, notably on incurable cancers.

The present invention therefore provides a compound of the following formula (I):

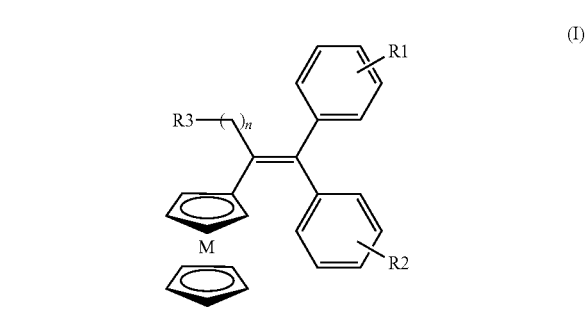

or a pharmaceutically acceptable salt or solvate thereof, a stereoisomer or a mixture of stereoisomers in any ratio, in particular a mixture of enantiomers, and more particularly a racemic mixture, or a water-soluble derivative, in which:
  M is Fe (iron), Ru (ruthenium) or Os (osmium), preferably Fe,
  n is an integer comprised between 1 and 8,
  R1 and R2 are, independently from each other, H, $CF_3$, CN, $OR^4$ or $NR^5R^6$, and
  R3 is $CO_2R^7$, $OR^8$ or $NR^9R^{10}$,
wherein:
  $R^4$ is H, ($C_1$-$C_6$)alkyl, —CO—($C_1$-$C_6$)alkyl or —$(CH_2)_m$ $NR^{11}R^{12}$,
  $R^5$, $R^6$, $R^{11}$ and $R^{12}$ are, independently from one another, H, ($C_1$-$C_6$)alkyl or —CO—($C_1$-$C_6$)alkyl, $R^7$ is H or $(C_1-C_6)$alkyl,
$R^8$ is H, $(C_1-C_6)$alkyl or —CO—$(C_1-C_6)$alkyl,
$R^9$ and $R^{10}$ are, independently from one another, H, $(C_1-C_6)$alkyl or —CO—$(C_1-C_6)$alkyl, or
$R^9$ and $R^{10}$ form together with the nitrogen atom bearing them a cycle of the following formula:

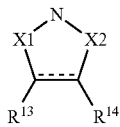

in which:

------ represents a single or double bond,

X1 and X2 are, independently from one another, C=O, $SO_2$, CH—$OR^{19}$, CH—$SR^{20}$, CH—$NR^{21}R^{22}$ or CH—$NHC(O)R^{23}$, $R^{13}$ and $R^{14}$ are, independently from one another, H or $(C_1-C_6)$alkyl, or $R^{13}$ and $R^{14}$ form together with the carbon atoms bearing them a 5- or 6-membered hydrocarbon cycle, $R^{19}$, $R^{20}$, $R^{21}$, and $R^{22}$ are, independently from one another, H or $(C_1-C_6)$alkyl, and $R^{23}$ is a $(C_1-C_6)$alkyl group, and m is an integer comprised between 1 and 8.

In the present invention, <<pharmaceutically acceptable>> should be understood as designating what is useful in the preparation of a pharmaceutical composition, what is generally safe, non toxic and neither biologically nor otherwise undesired, and what is acceptable both for veterinary use and human pharmaceutics.

The term <<pharmaceutically acceptable salt or solvate>> is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The term "stereoisomer", within the meaning of the present invention, should be understood as designating diastereoisomers or enantiomers. Stereoisomers which are not mirror images of each other are thus referred to as "diastereoisomers", and stereoisomers which are mirror images of each other but that cannot be superimposed are referred to as "enantiomers".

A carbon atom linked to four non identical substituents is referred to as a "chiral center". A molecule having such a chiral center is said to be chiral and has two enantiomer forms. A molecule having several chiral centers thus has several diastereoisomer and enantiomer forms.

An equimolar mixture of two enantiomers is called a racemic mixture.

The term "water-soluble derivative" should be understood as designating, within the meaning of the present invention, compounds of formula (I) according to the invention with an increased water-solubility and thus with an increased bio-availability. Such compounds will be in particular compounds of formula (I) in which at least one of R1, R2 and R3 represents an hydroxyl group esterified or coupled to a water-soluble species, such as a saccharide or a water-soluble polymer. Thus, in this case, at least one of R1, R2 and R3 represents an ester (—CO—$(C_1-C_6)$alkyl), a saccharidic moiety or a water-soluble polymer moiety bound to the rest of the molecule by means of an oxygen atom (for ex. —OCOCH$_2$A$^1$CH$_2$COA$^2$(CH$_2$CH$_2$O)$_p$CH$_2$CH$_2$A$^3$ as described below).

The term "saccharide" should be understood as including in particular, within the meaning of the present invention, erythrose, threose, ribose, arabinose, xylose, lyxose, allose, altrose, glucose, mannose, gulose, idose, galactose, talose, erythrulose, ribulose, xylulose, psicose, fructose, sorbose or also tagatose, either in D or L form. Advantageously, it is glucose or rhamnose.

The term "saccharidic moiety" as used in the present invention refers to a saccharide as defined above bound to the rest of the molecule by means of its oxygen atom present at the anomeric position.

The term "water-soluble polymer" should be understood as including in particular, within the meaning of the present invention, a dendrimer or a polyethylene glycol (PEG) derivative. A dendrimer can be in particular a polyamidoamide (PAMAM) type dendrimer.

A water-soluble polymer moiety can be notably a chain derived from PEG of the formula —COCH$_2$A$^1$CH$_2$COA$^2$(CH$_2$CH$_2$O)$_p$CH$_2$CH$_2$A$^3$, where:

$A^1$ represents a direct bond, 0, $CH_2$ or $CH_2$—$CH_2$, $A^2$ represents 0 or NH, $A^3$ represents $OR^{15}$ or $NR^{16}R^{17}$, $R^{15}$, $R^{16}$ and $R^{17}$ are, independently from each other, H or $(C_1-C_6)$alkyl, and p is an integer comprised between 1 and 20.

The term "$(C_1-C_6)$alkyl" should be understood as designating, within the meaning of the present invention, a saturated, linear or branched hydrocarbon group having from 1 to 6 carbon atoms, and advantageously from 1 to 4 carbon atoms, in particular methyl, ethyl, n-propyl, isopropyl, n-butyl, iso-butyl, sec-butyl and tent-butyl groups.

The term "5- or 6-membered hydrocarbon cycle" should be understood as designating, within the meaning of the present invention, a 5- or 6-membered saturated, unsaturated or aromatic hydrocarbon cycle. It can be in particular a phenyl ring.

The term "aryl", as used in the present invention, refers to an aromatic hydrocarbon group comprising preferably 6 to 10 carbon atoms and comprising one or more fused rings, such as, for example, a phenyl or naphtyl group. Advantageously, it will be a phenyl group.

The term "aryl-$(C_1$-$C_6)$alkyl", as used in the present invention, refers to an aryl group as defined above bound to the molecule via a $(C_1$-$C_6)$alkyl group as defined above. In particular, it is a benzyl group.

The term "$(C_1$-$C_6)$alkyl-aryl", as used in the present invention, refers to a $(C_1$-$C_6)$alkyl group as defined above bound to the molecule via an aryl group as defined above. In particular, it can be a tolyl group ($CH_3Ph$).

The term "halogen" should be understood, within the meaning of the present invention, as being a fluorine, bromine, chlorine or iodine atom.

According to a preferred embodiment, M represents an iron atom Fe.

According to a particular embodiment, n is comprised between 2 and 6, notably between 2 and 5.

According to a particular embodiment, R1 and R2 are, independently from each other, H, $OR^4$ or $NR^5R^6$.

Advantageously, at least one of R1 and R2 is not a hydrogen, even more advantageously R1 is not a hydrogen, and notably both R1 and R2 are not a hydrogen.

In particular, at least one of R1 and R2 is $OR^4$ or $NR^5R^6$, and the other is notably H, $OR^4$ or $NR^5R^6$, preferably $OR^4$ or $NR^5R^6$.

In a preferred embodiment, at least one of R1 and R2 is $OR^4$, and the other is notably H or $OR^4$, preferably $OR^4$, with $R^4$ as defined above and notably with $R^4$=H. In one further embodiment, R1 and/or R2 are/is located in the para position on the phenyl ring, in particular R1 is located in the para position on the phenyl ring. Advantageously, R1 and R2 are located in the para position on the phenyl ring and then the compounds of the present invention have the following formula (Ia) or preferably (Ia-Fe):

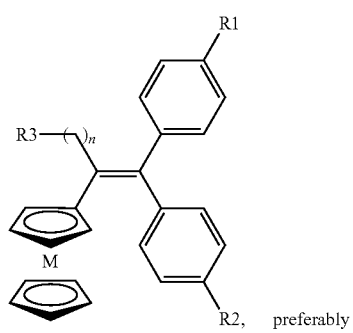

(Ia)

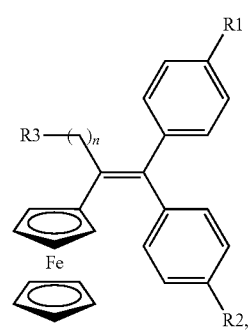

(Ia-Fe)

in which n, R1, R2 and R3 are as defined above, and notably with at least one of R1 and R2, and preferably R1 and R2, being $OR^4$ or $NR^5R^6$, advantageously $OR^4$, and preferably OH.

According to a particular embodiment, R1 and R2 are identical.

R3 is $CO_2R^7$, $OR^8$ or $NR^9R^{10}$.

$R^7$ can be in particular $(C_1$-$C_6)$alkyl.

$R^8$ can be in particular H.

At least one of $R^9$ and $R^{10}$ can be in particular, independently from one another, —CO—$(C_1$-$C_6)$alkyl, or $R^9$ and $R^{10}$ can form together with the nitrogen atom bearing them a cycle of the following formula:

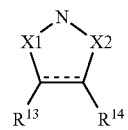

in which ——, X1, X2, $R^{13}$ and $R^{14}$ are as defined above, and preferably at least one of X1 and X2 is C=O. Notably X1 and X2 are, independently from one another, C=O or CH—$OR^{19}$, and preferably at least one of X1 and X2 is C=O, the other being C=O or CH—$OR^{19}$.

According to a particular embodiment, R3 is $CO_2$—$(C_1$-$C_6)$alkyl, OH or $NR^9R^{10}$ with at least one of $R^9$ and $R^{10}$ being, independently from one another, —CO—$(C_1$-$C_6)$alkyl, or $R^9$ and $R^{10}$ forming together with the nitrogen atom bearing them a cycle of the following formula:

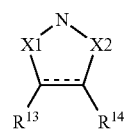

in which ——, X1, X2, $R^{13}$ and $R^{14}$ are as defined above, and preferably at least one of X1 and X2 is C=O. Notably X1 and X2 are, independently from one another, C=O or CH—$OR^{19}$, and preferably at least one of X1 and X2 is C=O, the other being C=O or CH—$OR^{19}$.

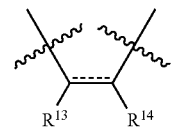

can be in particular

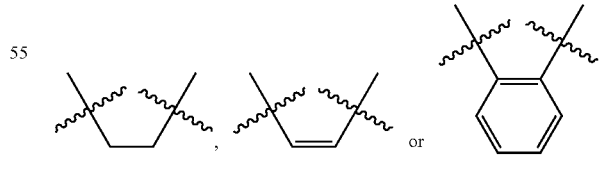

The compound according to the present invention can be selected in particular from compounds P64, P49, P189, P188, P504, P680, P632, P110, P53, P536, P537, P681, P651, P54, P697, P686, P720, P722, P723, P710, P721, P727, W2 and W3 described in the experimental part below, as well as pharmaceutically acceptable salts and solvates thereof.

The present invention concerns also a compound of formula (I) as defined above for use as a medicine, in particular in the treatment of cancer.

The present invention further relates to the use of a compound of formula (I) as defined above for the manufacture of a medicine, especially intended for the treatment of cancer.

The present invention further relates to a method for the treatment of cancer comprising administering an effective amount of a compound of formula (I) as defined above to a patient in need thereof.

The cancer can be chosen among gliomas, melanomas (notably uveal melanomas), retinoblastomas, breast cancers (notably non-hormone-dependent breast cancers), prostate cancers, lung cancers (notably non-small-cell lung cancers), ovarian cancers, esophageal cancers, liver cancers, pancreatic cancers, head and neck cancers, colon cancers and kidney cancers.

The present invention concerns also a pharmaceutical composition comprising at least one compound of formula (I) as defined above, in combination with at least one pharmaceutically acceptable vehicle.

This pharmaceutical composition can include at least one additional active ingredient, which can be in particular an anticancer compound advantageously selected from 6-mercaptopurin, fludarabin, cladribin, pentostatin, cytarabin, 5-fluorouracil, gemcitabin, methotrexate, raltitrexed, irinotecan, topotecan, etoposide, daunorubicin, doxorubicin, epirubicin, idarubicin, pirarubicin, mitoxantrone, chlormethin, cyclophosphamide, Ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

The compounds according to the invention can be administered orally, sublingually, parenterally, subcutaneously, intramuscularly, intravenously, transdermally, topically or rectally.

In the pharmaceutical compositions of the present invention to be administered orally, sublingually, parenterally, subcutaneously, intramuscularly, intravenously, transdermally, topically or rectally, the active ingredient can be administered in unit dosage forms, as a mixture with conventional pharmaceutical carriers, to animals or humans. Suitable unit dosage forms include oral forms such as tablets, capsules, powders, granules, and oral solutions or suspensions, sublingual and buccal dosage forms, parenteral, subcutaneous, intramuscular, intravenous, intranasal or intraocular dosage forms, and rectal dosage forms.

For preparing a solid composition in the form of a tablet, the main active ingredient is mixed with a pharmaceutical vehicle such as gelatin, starch, lactose, magnesium stearate, talc, gum arabic or the like. The tablets can be coated with sucrose or other suitable materials or can also be processed in order to have an sustained or delayed activity and so as to continuously deliver a predetermined amount of active ingredient.

A preparation in the form of capsules is obtained by mixing the active ingredient with a diluent and by filling the resulting mixture into soft or hard gelatin capsules.

A preparation in the form of syrups or elixirs can contain the active ingredient together with a sweetener, an antiseptic agent, as well as a flavoring agent and a suitable colorant.

Water-dispersible powders or granules can contain the active ingredient in a mixture with dispersing agents or wetting agents, or suspending agents, as well as with taste modifiers or sweeteners.

For rectal administration, suppositories are employed which are prepared with binders melting at rectum temperature, for example cocoa butter or polyethylene glycols.

For parenteral, intranasal or intraocular administration, aqueous suspensions, isotonic saline solutions or sterile solutions for injection containing pharmacologically compatible dispersing agents and/or wetting agents are used.

The active ingredient can further be formulated in the form of microcapsules or nanocapsules, optionally with one or more additive carriers.

The compounds of the invention can be used at daily doses in the range of between 0.01 mg and 1000 mg, taken in one single dosage once a day or divided into several individual doses given at intervals during the day, for example twice a day in equal doses. The daily dosage is advantageously in the range of between 5 mg and 500 mg, even more advantageously between 10 mg and 200 mg. It may be necessary to use dosages outside these ranges in a manner known to the person skilled in the art. The present invention concerns also a pharmaceutical composition comprising:
(i) at least one compound of formula (I) as defined above, and
(ii) at least one additional active ingredient,
as combination products to be administered simultaneously, separately or sequentially.

Indeed, dual- or tri-therapies are conventionally used for treating cancer. The active ingredient used is advantageously an anticancer compound.

Examples of active principles that can be combined with a compound of formula (I) in a composition according to the invention include but are not limited to 6-mercaptopurin, fludarabin, cladribin, pentostatin, cytarabin, 5-fluorouracil, gemcitabin, methotrexate, raltitrexed, irinotecan, topotecan, etoposide, daunorubicin, doxorubicin, epirubicin, idarubicin, pirarubicin, mitoxantrone, chlormethin, cyclophosphamide, ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, bicalutamide, cyproterone acetate, triptorelin, leuprorelin, goserelin, buserelin, formestan, aminoglutethimide, anastrazole, letrozole, tamoxifen, octreotide and lanreotide.

The present invention concerns also a pharmaceutical composition as defined above for use in the treatment of cancer.

The present invention further relates to a method for the treatment of cancer comprising administering an effective amount of a pharmaceutical composition as defined above to a patient in need thereof.

The present invention also relates to a compound of formula (I) as defined above for use as a medicine, in particular in the treatment of cancer, alone or in combination, simultaneously, separately or sequentially, with ionizing or non-ionizing radiations or with at least one additional active ingredient.

The present invention also relates to the use of a compound of formula (I) as defined above, for the manufacture of a medicine to be administered alone or in combination, simultaneously, separately or sequentially, with ionizing or non-ionizing radiations or with at least one additional active ingredient, in particular for the treatment of cancer.

The present invention further relates to a method for the treatment of cancer, comprising administering an effective amount of a compound of formula (I) as defined above, alone or in combination, simultaneously, separately or sequentially, with ionizing or non-ionizing radiations or with at least one additional active ingredient, to a patient in need thereof.

The radiations used can be in particular X rays or gamma rays, which radiations are commonly used in radiotherapy for the treatment of cancer.

The at least one additional active ingredient can be in particular an anticancer compound advantageously selected from 6-mercaptopurin, fludarabin, cladribin, pentostatin, cytarabin, 5-fluorouracil, gemcitabin, methotrexate, raltitrexed, irinotecan, topotecan, etoposide, daunorubicin, doxorubicin, epirubicin, idarubicin, pirarubicin, mitoxantrone, chlormethin, cyclophosphamide, ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

The cancer can be chosen among gliomas, melanomas (notably uveal melanomas), retinoblastomas, breast cancers (notably non-hormone-dependent breast cancers), prostate cancers, lung cancers (notably non-small-cell lung cancers), ovarian cancers, esophageal cancers, liver cancers, pancreatic cancers, head and neck cancers, colon cancers and kidney cancers.

The present invention also provides a first method for the preparation of a compound of formula (I) as defined above, in which R3 is $CO_2$—$(C_1$-$C_6)$alkyl or $OR^8$ with $R^8 \neq H$, comprising the following steps:
(i) McMurry coupling between a compound of the following formula (II):

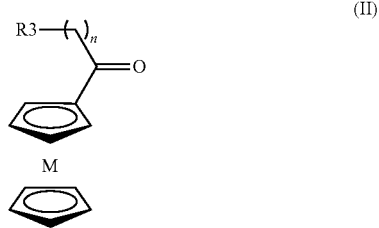

wherein M, n and R3 are as defined above,
and a compound of the following formula (III):

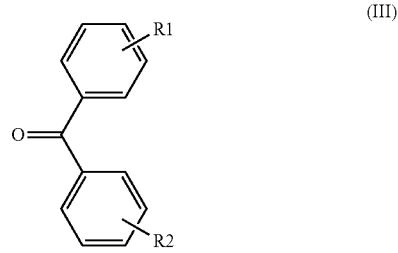

wherein R1 and R2 are as defined above, to give a compound of formula (I) as defined above, and
(ii) optionally salification or solvatation of the compound of formula (I) obtained in step (i) to give a pharmaceutically acceptable salt or solvate thereof Step (i):

McMurry coupling is described in particular in the following publications: Nakayama J. et al. Chem. Com. 1986, 12, 974-975; Top S. et al. Chem. Eur. J. 2003, 9, 5223-5236; Vessiéres A. et al. J. Med. Chem. 2005, 48, 3937-3940; or Hillard E. A. et al. Dalton Transactions 2007, 43, 5073-5081.

McMurry coupling employs as a reagent a titanium complex having a low valency number, such as $TiCl_4$ or $TiCl_3$, in the presence of a reducing agent, such as lithium, sodium, magnesium, zinc, $LiAlH_4$, or Zn—Cu amalgam.

Preferably, the McMurry coupling reaction is conducted in the presence of $TiCl_4$ and zinc, preferably in the form of a powder, and particularly in the presence of pyridine.

Said McMurry coupling can be optionally followed with a reaction of deprotection and/or modification and/or functionalization of R1, R2 and R3 by conventional methods well known to those skilled in the art.

The compounds of formula (II) can be obtained by methods well known to those skilled in the art and more particularly described in the following articles: Top, S. et al. Journal of Organometallic Chemistry 1997, 541(1-2), 355-361; Hillard, E. A. et al. Dalton Transactions 2007, 43, 5073-5081; Metay, E. et al. European Journal of Organic Chemistry 2008, 25, 4304-4312; Kumar, J. et al. Chemical Communications (Cambridge, United Kingdom) 2008, 22, 2526-2528; Ferreira, A. et al. Organometallics 2009, 28, 18, 5412-5423; M. Aslam Siddiqi et al. Materials 2010, 3, 1172-1185.

The compounds of formula (III) can be either commercially available, or prepared by methods well known to those skilled in the art. In particular, 4,4'-dihydroxybenzophenone is sold by Alfa Aesar.

Step (ii):

The salification or solvatation step can be carried out by methods well known to the one skilled in the art, in particular by reaction of the compound of formula (I) obtained in step (i) with a pharmaceutically acceptable acid (organic or inorganic acid), base (organic or inorganic acid) or solvent, as defined previously.

The solvent can be notably the solvent used in the last step of the preparation of the compound according to the invention, in particular the solvent used in step (i).

Thus steps (i) and (ii) can be carried out in a single step, without isolating intermediate compounds.

The present invention also provides a second method for the preparation of a compound of formula (I) as defined above, in which R3 is $OR^8$, comprising the following steps:
(a) reduction of a compound of the following formula (Ib):

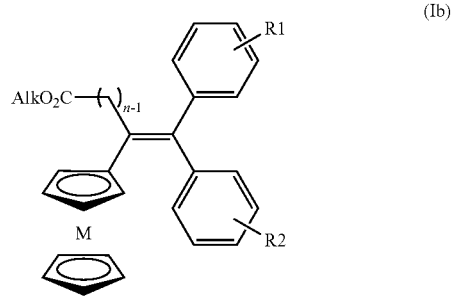

wherein M, n, R1 and R2 are as defined above and Alk is (C$_1$-C$_6$)alkyl, to give a compound of formula (I) in which R3 is OH, (b) optionally substitution of the compound obtained in step (a) to give a compound of formula (I) in which R3 is OR$^8$ with R$^8$≠H, and (c) optionally salification or solvatation of the compound of formula (I) obtained in step (a) or (b) to give a pharmaceutically acceptable salt or solvate thereof.

Step (a):

This step can be carried out in the presence of a reducing agent in conditions well known to the one skilled in the art. The reducing agent can be LiAlH$_4$. The reaction can be conducted in diethyl ether as solvent, notably under reflux.

The compound of formula (Ib) can be prepared notably by the first method described above.

Step (b):

This substitution step can be carried out in conditions well known to the one skilled in the art. Notably the reaction can be carried out by reacting a compound of formula (I) in which R3=OH with a compound of formula R$^8$-LG with R$^8$≠H and LG representing a leaving group, notably in the presence of a base.

The term "leaving group" as used in the present invention refers to a chemical group which can be easily replaced with a nucleophile during a nucleophile substitution reaction, the nucleophile being in the present case an alcohol, i.e. a molecule carrying a group OH. Such a leaving group can be in particular a halogen atom or a sulfonate. The sulfonate is in particular a group —OSO$_2$—R$_{18}$ with R$_{18}$ representing a (C$_1$-C$_6$)alkyl, aryl, aryl-(C$_1$-C$_6$)alkyl or (C$_1$-C$_6$)alkyl-aryl group, the said group being optionally substituted with one or several halogen atoms such as fluorine atoms. The sulfonate can be notably a mesylate (CH$_3$—S(O$_2$)O—), a triflate (CF$_3$—S(O)$_2$O—) or a tosylate (p-Me-C$_6$H$_4$—S(O)$_2$O—).

Step (c): See Step (ii).

The present invention also provides a third method for the preparation of a compound of formula (I) as defined above, in which R3 is COOH, comprising the following steps:

(1) saponification of a compound of the following formula (Ic):

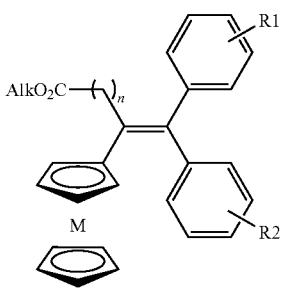

wherein M, n, R1 and R2 are as defined above and Alk is (C$_1$-C$_6$)alkyl, to give a compound of formula (I) in which R3 is COOH, and (2) optionally salification or solvatation of the compound of formula (I) obtained in step (1) to give a pharmaceutically acceptable salt or solvate thereof.

Step (1):

This step can be carried out in conditions well known to the one skilled in the art. Notably, the reaction can be carried out in the presence of K$_2$CO$_3$.

The compound of formula (Ib) can be prepared notably by the first method described above.

Step (2): See Step (ii).

The present invention also provides a third method for the preparation of a compound of formula (I) as defined above, in which R3 is NR$^9$R$^{10}$, comprising the following steps:

(A) reaction of a compound of the following formula (Id):

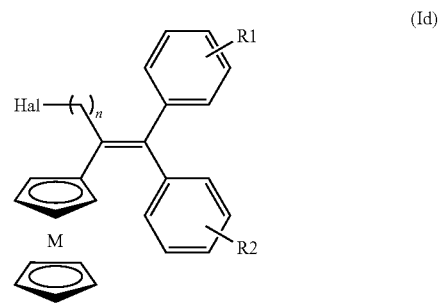

wherein M, n, R1 and R2 are as defined above and Hal is a halogen atom, with a compound of formula HNR$^9$R$^{10}$, to give a compound of formula (I) in which R3 is NR$^9$R$^{10}$, and (B) optionally salification or solvatation of the compound of formula (I) obtained in step (A) to give a pharmaceutically acceptable salt or solvate thereof.

Step (A):

This step can be carried out in conditions well known to the one skilled in the art, notably in the presence of a base such as K$_2$CO$_3$.

The compound of formula (Id) can be prepared notably by a McMurry coupling reaction as described above or as described in the following article: Hillard et al. *J. Organomet. Chem.* 2007, 692, 1315-1326.

Step (B): See Step (ii).

Further functionalization/protection/deprotection steps can be carried out in the processes described above, such steps and their reaction conditions being well known to the one skilled in the art.

The compound of the invention may be recovered from the reaction medium by methods well known to those skilled in the art, especially by filtration or evaporation of the solvent, especially under vacuum. Washing steps of the organic layer containing the compound of the invention and extraction steps can be carried out beforehand.

The product obtained can be purified if necessary by conventional purification methods well known to those skilled in the art, such as by recrystallization, preparative thin layer chromatography, high performance liquid chromatography (commonly known as HPLC) or silica gel column chromatography. Advantageously, the preferred method is recrystallization when the product is crystalline and/or silica gel column chromatography.

The following examples are intended to better illustrate the present invention but are not to be construed as limiting its scope.

EXAMPLES

Abbreviations used:
CI Chemical ionisation
DCM Dichloromethane
DMF Dimethylformamide DMSO Dimethylsulfoxide
EI Electron ionisation
ESI Electrospray ionisation
Et Ethyl
HRMS High Resolution Mass Spectrometry
IR Infra Red
Me Methyl
MS Mass Spectrometry
NMR Nuclear Magnetic Resonance
PE Petroleum ether
THF Tetrahydrofuran
TLC Thin Layer Chromatography Example 1: Preparation of Compounds of the Invention 1.1. Preparation of Ester Derivatives

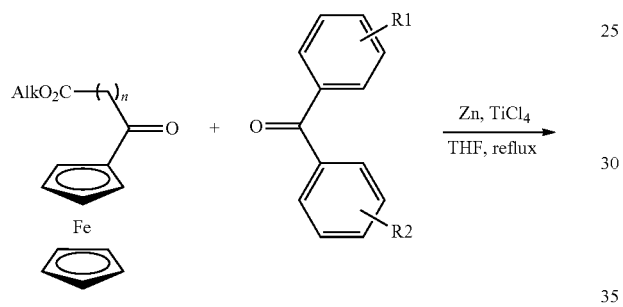

with Alk=($C_1$-$C_6$)alkyl and n, R1 and R2 as defined above.

General Protocol (Reaction of McMurry):

Titanium chloride was added dropwise to a suspension of zinc powder in dry THF at 10° C. The mixture was heated at reflux for 2 hours. A second solution was prepared by dissolving the corresponding ketone (equimolar) in dry THF. This latter solution was added dropwise to the first solution and then the reflux was continued for 2 hours or more. After cooling to room temperature, the mixture was stirred with water and dichloromethane. The mixture was acidified with diluted hydrochloric acid until dark color disappeared and was decanted. The aqueous layer was extracted with dichloromethane and the combination of organic layers was dried on magnesium sulphate. After concentration under reduced pressure, the crude product was chromatographed on silica gel column with a mixture of cyclohexane/ethyl acetate as the eluent.

Ethyl 3-ene-3-ferrocenyl-4,4-bis-(4-hydroxyphenyl)-butanoate, P64

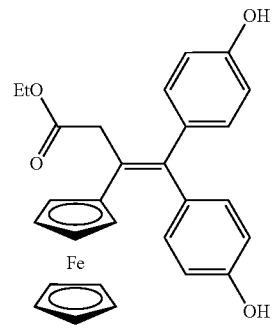

Yield: 40%. $^1$H NMR (acetone $D_6$): δ 1.23 (t, J=7.2 Hz, 3H, $CH_3$), 3.65 (s, 2H, $CH_2$), 3.93 (t, J=2.0 Hz, 2H, $C_5H_4$), 4.09 (q, J=7.2 Hz, 2H, $CH_2O$), 4.11 (t, J=2.0 Hz, 2H, $C_5H_4$), 4.17 (s, 5H, Cp), 6.76 (d, J=8.7 Hz, 2H, $C_6H_4$), 6.83 (d, J=8.7 Hz, 2H, $C_6H_4$), 6.97 (d, J=8.7 Hz, 2H, $C_6H_4$), 7.10 (d, J=8.7 Hz, 2H, $C_6H_4$), 8.31 (s, 1H, OH), 8.33 (s, 1H, OH). $^{13}$C NMR (acetone $D_6$): δ 15.3 ($CH_3$), 44.1 ($CH_2$), 61.5 ($CH_2$), 69.5 (2CH $C_5H_4$), 70.6 (5 CH Cp), 70.7 (2 CH $C_5H_4$), 88.8 (C $C_5H_4$), 116.5 (2 CH $C_6H_4$), 116.6 (2 CH $C_6H_4$), 128.9 (C), 131.8 (2 CH $C_6H_4$), 132.4 (2 CH $C_6H_4$), 137.2 (C), 137.3 (C), 142.8 (C), 157.7 (2 C), 173.2 (CO). IR (KBr, ν $cm^{-1}$): 3361 (OH), 2933, 2986, 3035 ($CH_2$,$CH_3$), 1682 (CO). MS (CI, $NH_3$) m/z: 483 $[M+H]^+$, 500 $[M+NH_4]^+$. HRMS (CI, $NH_3$, $C_{28}H_{27}FeO_4$: $[M+H]^+$) calcd: 483.1259. found: 483.1265. Anal. Calcd for $C_{28}H_{26}FeO_4$: C, 69.72; H, 5.43. Found: C, 69.63; H, 5.45.

Ethyl 4-ene-4-ferrocenyl-5,5-bis-(4-hydroxyphenyl)-pentanoate, P49

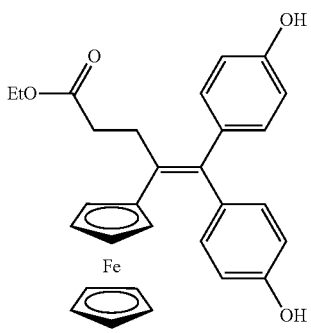

Yield: 51%. $^1$H NMR (acetone $D_6$): δ 1.22 (t, J=7.2 Hz, 3H, $CH_3$), 2.44 (t, J=8.2 Hz, 2H, $CH_2$), 2.98 (t, J=8.2 Hz, 2H, $CH_2$), 3.99 (t, J=1.9 Hz, 2H, $C_5H_4$), 4.07 (q, J=7.1 Hz, 2H, $CH_2O$), 4.12 (t, J=1.9 Hz, 2H, $C_5H_4$), 4.18 (s, 5H, Cp), 6.74 (d, J=8.7 Hz, 2H, $C_6H_4$), 6.87 (d, J=8.7 Hz, 2H, $C_6H_4$), 6.90 (d, J=8.7 Hz, 2H, $C_6H_4$), 7.11 (d, J=8.7 Hz, 2H, $C_6H_4$), 8.26 (s, 1H, OH), 8.32 (s, 1H, OH). $^{13}$C NMR (acetone $D_6$): δ 14.6 ($CH_3$), 30.9 ($CH_2$), 35.4 ($CH_2$), 60.6 ($CH_2$), 68.8 (2 CH $C_5H_4$), 69.9 (5 CH Cp), 70.0 (2 CH $C_5H_4$), 88.1 (C $C_5H_4$), 115.8 (2 CH $C_6H_4$), 116.0 (2 CH $C_6H_4$), 131.2 (2 CH $C_6H_4$), 131.8 (2 CH $C_6H_4$), 133.5 (C), 136.7 (C), 137.2 (C), 140.2 (C), 156.8 (2 C), 173.3 (CO). IR (KBr, ν $cm^{-1}$): 3330, 3396 (OH), 2986, 3026, 3058, 3094 ($CH_2$,$CH_3$), 1690 (CO). MS (EI, 70 eV) m/z: 496 [M]+, 451 [M-OEt]+, 431 [M-Cp]+, 121 [FeCp]+. HRMS (EI, 70 eV, $C_{29}H_{28}FeO_4$: [M]+) calcd: 496.1337. found: 496.1331. Anal. Calcd for $C_{29}H_{28}FeO_4$: C, 70.17; H, 5.68. Found: C, 69.89; H, 5.66.

Methyl 4-ene-4-ferrocenyl-5,5-bis-(4-hydroxyphenyl)-pentanoate, P189

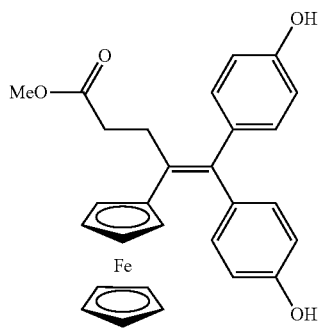

Yield: 94%. $^1$H NMR (acetone $D_6$): δ 6 2.46 (t, J=8.2 Hz, 2H, $CH_2$), 2.98 (t, J=8.2 Hz, 2H, $CH_2$), 3.43 (s, 3H, $CH_3$), 3.98 (t, J=1.9 Hz, 2H, $C_5H_4$), 4.12 (t, J=1.9 Hz, 2H, $C_5H_4$), 4.18 (s, 5H, Cp), 6.74 (d, J=8.7 Hz, 2H, $C_6H_4$), 6.86 (d, J=8.7 Hz, 2H, $C_6H_4$), 6.89 (d, J=8.7 Hz, 2H, $C_6H_4$), 7.11 (d, J=8.7 Hz, 2H, $C_6H_4$), 8.29 (s, 1H, OH), 8.35 (s, 1H, OH). $^{13}$C NMR (acetone $D_6$): δ 31.7 ($CH_2$), 35.9 ($CH_2$), 52.3 ($CH_3$), 68.6 (2 CH $C_5H_4$), 70.6 (5 CH Cp), 70.7 (2 CH $C_5H_4$), 88.8 (C $C_5H_4$), 116.6 (2 CH $C_6H_4$), 116.8 (2 CH $C_6H_4$), 131.9 (2 CH $C_6H_4$), 132.5 (2 CH $C_6H_4$), 134.2 (C), 137.4 (C), 137.9 (C), 141.1 (C), 157.6 (2 C), 174.4 (CO). IR (KBr, ν cm$^{-1}$): 3393 (OH), 3098, 3031, 2953 ($CH_2$, $CH_3$), 1698 (CO). MS (EI, 70 eV) m/z: 482 [M]', 451 [M-OMe]+, 121 [CpFe]+. HRMS (FAB, $C_{28}H_{26}FeO_4$: [M]+) calcd: 482.1181. found: 482.1196. Anal. Calcd for $C_{28}H_{26}FeO_4$: C, 69.72; H, 5.43. Found: C, 69.79; H, 5.56.

Methyl 5-ene-5-ferrocenyl-6,6-bis-(4-hydroxyphenyl)-hexanoate, P188

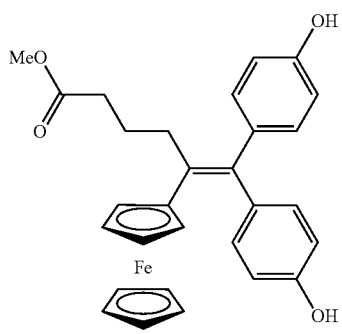

Yield: 12%. $^1$H NMR (DMSO $D_6$): δ 1.63-1.78 (m, 2H, $CH_2$), 2.23 (t, J=8.2 Hz, 2H, $CH_2$), 3.31-3.39 (m, 2H, $CH_2$), 3.57 (s, 3H, $CH_3$), 3.89 (t, J=1.9 Hz, 2H, $C_5H_4$), 4.11 (t, J=1.9 Hz, 2H, $C_5H_4$), 4.13 (s, 5H, Cp), 6.66 (d, J=8.5 Hz, 2H, $C_6H_4$), 6.75 (d, J=8.5 Hz, 2H, $C_6H_4$), 6.81 (d, J=8.5 Hz, 2H, $C_6H_4$), 6.98 (d, J=8.5 Hz, 2H, $C_6H_4$), 9.30 (s, 1H, OH), 9.34 (s, 1H, OH). $^{13}$C NMR (DMSO $D_6$): δ 26.4 ($CH_2$), 34.2 ($CH_2$), 34.3 ($CH_2$), 52.1 ($CH_3$), 68.7 (2 CH $C_5H_4$), 69.6 (2 CH $C_5H_4$), 69.9 (5 CH Cp), 87.6 (C $C_5H_4$), 115.9 (2×2 CH $C_6H_4$), 130.8 (2 CH $C_6H_4$), 131.3 (2 CH $C_6H_4$), 133.9 (C), 136.1 (C), 136.5 (C), 139.3 (C), 156.5 (C), 156.6 (C), 174.1 (CO). IR (KBr, ν cm$^{-1}$): 3420 (OH), 3028, 2948 ($CH_2$, $CH_3$), 1706, 1693 (CO). MS (CI, $NH_3$) m/z: 497 [M+H]+, 514 [M+$NH_4$]+. HRMS (CI, $NH_3$, $C_{29}H_{29}FeO_4$: [M+H]+) calcd: 497.1416. found: 497.1430. Anal. Calcd for $C_{29}H_{28}FeO_4$: C, 70.17; H, 5.68. Found: C, 69.96; H, 5.71.

Methyl 6-ene-6-ferrocenyl-7,7-bis-(4-hydroxyphenyl)-heptanoate, P504

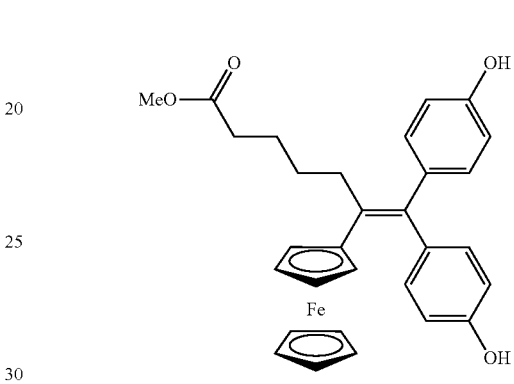

Yield: 39%. $^1$H NMR (acetone $D_6$): δ 1.49-1.60 (m, 4H, $CH_2$), 2.21 (t, J=6.8 Hz, 2H, $CH_2$), 2.67 (t, J=7.4 Hz, 2H, $CH_2$), 3.63 (s, 3H, $CH_3$), 3.97 (t, J=1.9 Hz, 2H, $C_5H_4$), 4.11 (t, J=1.9 Hz, 2H, $C_5H_4$), 4.17 (s, 5H, Cp), 6.74 (d, J=8.7 Hz, 2H, $C_6H_4$), 6.85 (d, J=8.7 Hz, 2H, $C_6H_4$), 6.90 (d, J=8.7 Hz, 2H, $C_6H_4$), 7.08 (d, J=8.7 Hz, 2H, $C_6H_4$), 8.24 (s, 1H, OH), 8.28 (s, 1H, OH). $^{13}$C NMR (acetone $D_6$): δ 26.5 ($CH_2$), 31.6 ($CH_2$), 34.8 ($CH_2$), 35.8 ($CH_2$), 52.2 ($CH_3$), 69.4 (2 CH $C_5H_4$), 70.7 (5 CH Cp), 70.8 (2 CH $C_5H_4$), 89.2 (C $C_5H_4$), 116.5 (2 CH $C_6H_4$), 116.6 (2 CH $C_6H_4$), 132.1 (2 CH $C_6H_4$), 132.5 (2 CH $C_6H_4$), 133.1 (C), 135.8 (C), 137.9 (C), 138.2 (C), 156.5 (C), 157.5 (C), 180.5 (CO). MS (ESI) m/z: 510 [M]+, 271, 143, 83. HRMS (ESI, $C_{30}H_{30}FeO_4$: [M]+) calcd: 510.1493. found: 510.1509.

Methyl 4-ene-4-ferrocenyl-5-(4-hydroxyphenyl)-5-phenyl-pentanoate, P680

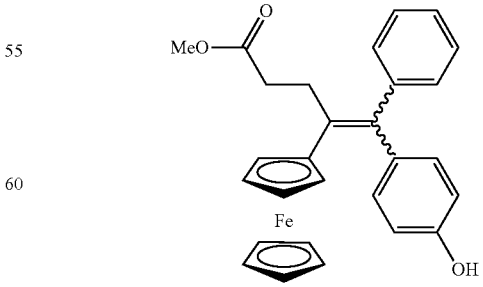

The Z and E isomers were separated by preparative HPLC (reverse phase with acetonitrile/water 90/10 as the eluent)

but totally converted into the 50/50 mixture in less than 12 hours. It was used as a 50/50 mixture of Z and E isomers for the tests.

Yield: 36%. $^1$H NMR (acetone D$_6$): δ 2.43-2.536 (m, 2H, CH$_2$), 2.87-3.05 (m, 2H, CH$_2$), 3.60 and 3.61 (s, 3H, CH$_3$), 3.92 and 3.99 (t, J=1.9 Hz, 2H, C$_5$H$_4$), 4.11 and 4.15 (t, J=1.9 Hz, 2H, C$_5$H$_4$), 4.18 and 4.19 (s, 5H, Cp), 6.76 and 6.87 (d, J=8.7 Hz, 2H, C$_6$H$_4$), 6.90-7.44 (m, 7H, C$_6$H$_4$), 8.34 and 8.39 (s, 1H, OH). $^{13}$C NMR (acetone D$_6$): δ 31.1 (CH$_2$), 35.8 and 35.9 (CH$_2$), 52.3 (CH$_3$), 69.7 (2 CH C$_5$H$_4$), 70.7 (5 CH Cp+2 CH C$_5$H$_4$), 88.1 and 88.2 (C C$_5$H$_4$), 116.7 and 116.9 (2 CH C$_6$H$_4$), 127.8 and 127.9 (CH C$_6$H$_5$), 129.7 and 130.0 (2 CH$_{arom}$), 130.7 and 131.3 (2 CH$_{arom}$), 131.9 and 132.4 (2 CH$_{arom}$), 134.9 and 135.3 (C), 136.8 and 137.0 (C), 141.0 (C), 146.3 and 146.7 (C), 157.7 (C), 174.3 and 174.4 (CO). MS (CI, NH$_3$) m/z: 467 [M+H]$^+$, 484 [M+NH$_4$]$^+$. HRMS (ESI, C$_{28}$H$_{26}$FeO$_3$: [M]$^+$) calcd: 466.1231. found: 466.1235.

Methyl 5,5-bis-[4-(3-dimethylaminopropoxy)phenyl]-4-ene-4-ferrocenyl pentanoate, P632

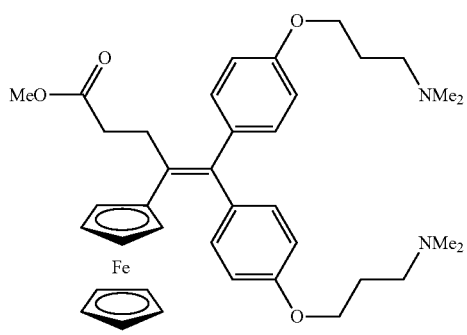

Protocol for the Preparation of Diamines of Type P632:

P189 (2.23 g) was dissolved into 50 mL of DMF and sodium hydride (0.74 g) was added portionwise. The mixture was stirred and then 3-dimethylamino-1-propyl chloride hydrochloride (1.10 g) was added. The mixture was refluxed overnight, cooled and after addition of 3 mL of ethanol was concentrated under reduced pressure. The residue was extracted with a mixture of diethyl ether and water and then was decanted. The organic layer was washed twice with a diluted aqueous solution of sodium hydroxide then with water, dried over magnesium sulphate and concentrated under reduced pressure. The residue was chromatographed on a silica gel column with acetone/triethylamine 10/1 as the eluent to give P632 as an oil with a 67% yield.

$^1$H NMR (CDCl$_3$): δ 1.99-2.13 (m, 4H, 2 CH$_2$), 2.36 (s, 6H, NMe$_2$), 2.38 (s, 6H, NMe$_2$), 2.44-2.65 (m, 6H, 2 CH$_2$N+CH$_2$), 2.95-3.04 (m, 2H, CH$_2$), 3.72 (s, 3H, OCH$_3$), 4.00 (t, J=1.9 Hz, 2H, CH C$_5$H$_4$), 4.05 (t, J=6.5 Hz, 2H, 2 CH$_2$O), 4.10 (t, J=6.5 Hz, 2H, 2 CH$_2$O), 4.17 (t, J=1.9 Hz, 2H, CH C$_5$H$_4$), 4.21 (s, 5H, Cp), 6.82 (d, J=8.7 Hz, 2H, C$_6$H$_4$), 6.94 (d, J=8.7 Hz, 2H, C$_6$H$_4$), 7.00 (d, J=8.7 Hz, 2H, C$_6$H$_4$), 7.17 (d, J=8.7 Hz, 2H, C$_6$H$_4$). $^{13}$C NMR (acetone D$_6$): δ 29.0 (2 CH$_2$), 31.7 (CH$_2$), 35.8 (CH$_2$), 46.5 (2 NMe$_2$), 52.3 (OCH$_3$), 57.6 (2 CH$_2$N), 67.4 (2 CH$_2$O), 69.7 (2 CH C$_5$H$_4$), 70.7 (5 CH Cp+2 CH C$_5$H$_4$), 88.5 (C C$_5$H$_4$), 115.6 (2 CH C$_6$H$_4$), 115.9 (2 CH C$_6$H$_4$), 131.9 (2 CH C$_6$H$_4$), 132.4 (2 CH C$_6$H$_4$), 134.7 (C), 138.3 (C), 138.7 (C), 140.5 (C), 159.5 (2 C). IR (KBr, ν cm$^{-1}$): 3091, 3031, 2953, 2857, 2811, 2761 (CH$_2$, CH$_3$), 1737 (CO). MS (EI, 70 eV) mh: 652 [M]$^+$, 86 [CH$_2$CH$_2$CH$_2$NMe$_2$]$^+$, 58 [CH$_2$NMe$_2$]$^+$. HRMS (ESI, C$_{38}$H$_{48}$FeN$_2$O$_4$: [M]$^+$) calcd: 652.2963. found: 652.2952.

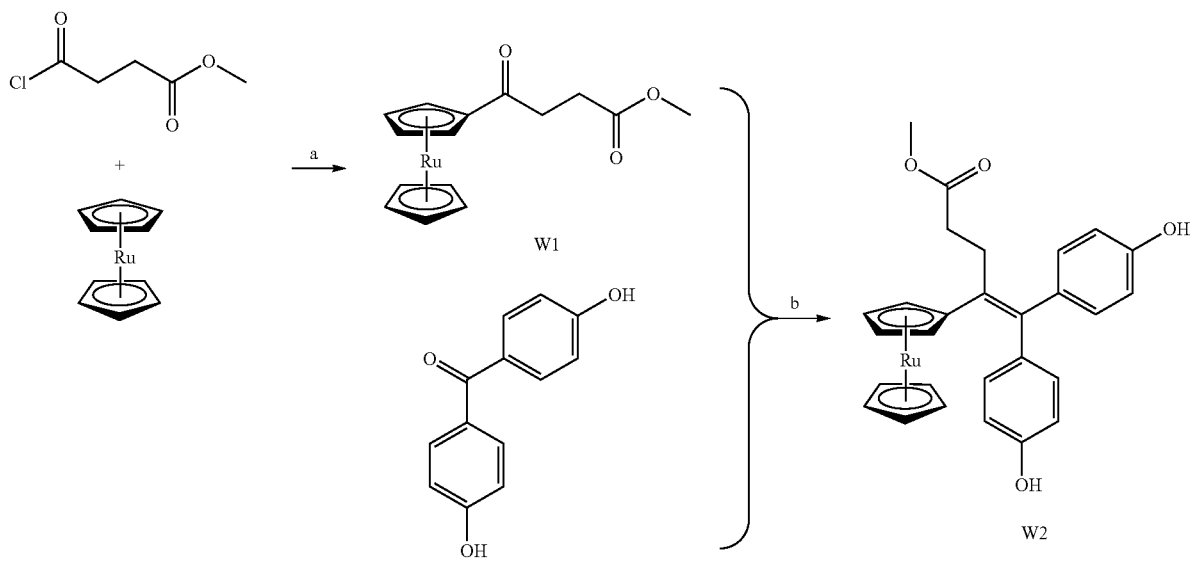

Synthesis of methyl 4-oxo-4-ruthenocenylbutanoate (W1)

(prepared according to M. Aslam Siddiqi et al. *Materials* 2010, 3, 1172-1185) $AlCl_3$ (0.8 g, 6 mmol) was added slowly to the solution of ruthenocene (1.3 g, 6 mmol) in 15 ml of DCM. 0.34 ml methyl 4-chloro-4-oxobutanoate (6 mmol) was added dropwise to the first solution and the resulting mixture was stirred for 12 hrs. Then the reaction was quenched by water. The aqueous layer was extracted three times with dichloromethane. The organic layer was dried over $MgSO_4$ and evaporated. The residue was purified by column chromatography on silica gel eluting with PE:EtOAc (6:1) to give methyl 4-oxo-4-ruthenocenyl butanoate as a light yellow solid 0.9 g, yield 43%. $^1$H NMR (300 MHz, $CDCl_3$): δ 2.64 (t, J=6.7 Hz, 2H, $CH_2$), 2.98 (t, J=6.7 Hz, 2H, $CH_2$), 3.70 (s, 3H, $OCH_3$), 4.62 (s, 5H, $C_5H_5$), 4.78 (t, J=3.0 Hz, 2H, $C_5H_4$), 5.13 (t, J=3.0 Hz, 2H, $C_5H_4$).

Synthesis of methyl 4-ene-5,5-bis-(4-hydroxyphenyl)-4-ruthenocenyl-pentanoate (W2)

$TiCl_4$ (0.6 ml, 5.5 mmol) was added dropwise to a suspension of zinc powder (0.6 g, 9.2 mmol) in 8 ml of THF at 0° C. The dark grey mixture obtained was heated at reflux for 2 h. A solution of THF (8 ml) containing 4,4'-dihydroxybenzophenone (0.65 g, 3 mmol) and methyl 4-oxo-4-ruthenocenylbutanoate (0.47 g, 1.36 mmol) was added dropwise to the first solution and the resulting mixture was heated for 2 h. After cooling to room temperature, the mixture was acidified by addition of diluted HCl. The aqueous layer was extracted with EtOAc for three times. The combined organic layer was dried over $MgSO_4$ and evaporated. The residue was purified by column chromatography on silica gel eluting with PE:EtOAc (2:1) to give methyl 4-ene-5,5-bis-(4-hydroxyphenyl)-4-ruthenocenyl-pentanoate as a light yellow solid 613 mg, yield 85%. $^1$H NMR (300 MHz, Acetone-$d_6$) δ 2.45 (t, J=7.5 Hz, 2H, $CH_2$), 2.66 (t, J=7.5 Hz, 2H, $CH_2$), 3.56 (s, 3H, $OCH_3$), 4.34 (t, J=3.0 Hz, 2H, $C_5H_4$), 4.39 (t, J=3.0 Hz, 2H, $C_5H_4$), 4.54 (s, 5H, $C_5H_5$), 6.67 (d, J=8.6 Hz, 2H, $C_6H_4$), 6.79 (d, J=8.6 Hz, 2H, $C_6H_4$), 6.86 (d, J=8.6 Hz, 2H, $C_6H_4$), 6.99 (d, J=8.5 Hz, 2H, $C_6H_4$), 8.21 (s, 1H, OH), 8.28 (s, 1H, OH); $^{13}$C NMR (75 MHz, Acetone-$d_6$) δ 32.4 ($CH_2$), 35.1 ($CH_2$), 51.5 ($OCH_3$), 70.4 (2 CH $C_5H_4$), 71.8 (5 CH $C_5H_5$), 72.8 (2 CH $C_5H_4$), 93.4 (C $C_5H_4$), 115.9 (2 CH $C_6H_4$), 115.5 (2 CH $C_6H_4$), 131.9 (2 CH, $C_6H_4$), 131.1 (2 CH, $C_6H_4$), 132.3 (2 C C=C), 136.8 (C $C_6H_4$), 140.7 (C $C_6H_4$), 156.9 (C $C_6H_4$), 156.7 (C $C_6H_4$), 173.8 (C CO).

1.2. Preparation of Halogenated Derivatives (Comparative Examples)

Protocol:

The chlorinated and brominated compounds have been prepared based on the McMurry protocol as described above for ester derivatives, starting from the corresponding chlorinated and brominated ketones.

5-chloro-2-ferrocenyl-1,1-bis-(4-hydroxyphenyl)-pent-1-ene, P687

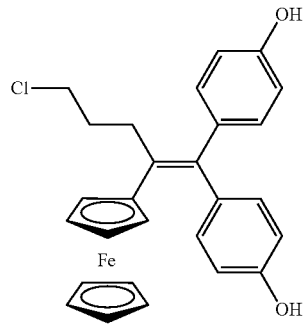

Yield: 68%. $^1$H NMR (acetone $D_6$): δ 1.89-2.02 (m, 2H, $CH_2$), 2.84 (t, J=8.0 Hz, 2H, $CH_2$), 3.54 (t, J=8.0 Hz, 2H, $CH_2$), 4.00 (t, J=1.9 Hz, 2H, CH $C_5H_4$), 4.12 (t, J=1.9 Hz, 2H, CH $C_5H_4$), 4.17 (s, 5H, Cp), 6.74 (d, J=8.7 Hz, 2H, $C_6H_4$), 6.86 (d, J=8.7 Hz, 2H, $C_6H_4$), 6.90 (d, J=8.7 Hz, 2H, $C_6H_4$), 7.10 (d, J=8.7 Hz, 2H, $C_6H_4$), 8.29 (s, 1H, OH), 8.34 (s, 1H, OH). $^{13}$C NMR (acetone $D_6$): δ 33.8 ($CH_2$), 35.1 ($CH_2$), 46.7 ($CH_2Cl$), 69.5 (2 CH $C_5H_4$), 70.6 (5CH Cp), 70.7 (2 CH $C_5H_4$), 89.1 (C $C_5H_4$), 116.5 (2 CH $C_6H_4$), 116.7 (2 CH $C_6H_4$), 132.0 (2 CH $C_6H_4$), 132.5 (2 CH $C_6H_4$), 134.7 (C), 137.6 (C), 138.0 (C), 140.7 (C), 157.5 (C). IR (KBr, ν $cm^{-1}$): 3433 (OH), 3085, 2951, 2868 (CH, $CH_2$). MS (CI, $NH_3$) m/z: 473 [M+H]$^+$. HRMS (ESI, $C_{27}H_{25}ClFeO_2$: [M]$^+$) calcd: 472.0892. found: 472.0887.

6-chloro-2-ferrocenyl-1,1-bis-(4-hydroxyphenyl)-hex-1-en, P719

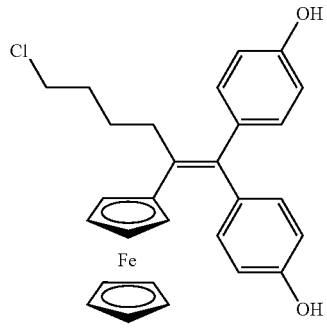

Yield: 60%. $^1$H NMR (acetone $D_6$): δ 1.61-1.74 (m, 4H, $CH_2$—$CH_2$); 2.69 (t, J=7.4 Hz, 2H, $CH_2$—C=C); 3.50 (t, J=6.2 Hz, 2H, $CH_2Cl$); 3.96 (t, J=1.9 Hz, 2H, H $C_5H_4$); 4.09 (t, J=1.9 Hz, 2H, H $C_5H_4$); 4.15 (s, 5H, HCp); 6.74 (d, J=8.6 Hz, 2H, H $C_6H_4$); 6.85 (d, J=8.6 Hz, 2H, H $C_6H_4$); 6.91 (d, J=8.6 Hz, 2H, H $C_6H_4$); 7.09 (d, J=8.6 Hz, 2H, H $C_6H_4$); 8.28 (s, 1H, OH); 8.32 (s, 1H, OH). $^{13}$C NMR (acetone $D_6$): δ 28.4 ($CH_2$); 33.0 ($CH_2$); 34.2 ($CH_2$); 45.3 ($CH_2Cl$); 68.4 (2 CH $C_5H_4$); 69.6 (5 CH Cp); 69.7 (2 CH $C_5H_4$); 87.9 (C $C_5H_4$); 115.5 (2 CH $C_6H_4$); 115.6 (2 CH $C_6H_4$); 131.0 (2 CH $C_6H_4$); 131.5 (2 CH $C_6H_4$); 134.5 (C); 136.7 (C); 137.0 (C); 139.2 (C); 156.4 (C), 156.5 (C). IR (KBr, ν $cm^{-1}$): 3419 (OH), 2987, 2952, 2863 (CH, $CH_2$). MS (EI, 70 eV) m/z: 486 [M]$^+$, 421, 343, 286, 186. HRMS (ESI, $C_{28}H_{27}ClFeO_2$: [M]$^+$) calcd: 486.1049. found: 486.1058.

5-bromo-2-ferrocenyl-1,1-bis-(4-hydroxyphenyl)-pent-1-ene, P528

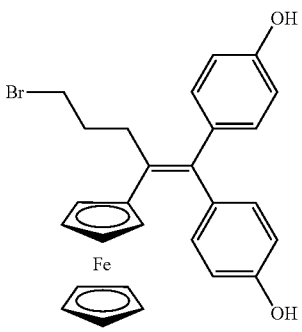

Yield: 71%. $^1$H NMR (acetone D$_6$): δ 1.96-2.10 (m, 2H, CH$_2$), 2.83 (t, J=7.9 Hz, 2H, CH$_2$), 3.38-3.49 (m, 2H, CH$_2$Br), 3.99 (t, J=1.9 Hz, 2H, CH C$_5$H$_4$), 4.11 (t, J=1.9 Hz, 2H, CH C$_5$H$_4$), 4.17 (s, 5H, Cp), 6.72 (d, J=8.7 Hz, 2H, C$_6$H$_4$), 6.84 (d, J=8.7 Hz, 2H, C$_6$H$_4$), 6.88 (d, J=8.7 Hz, 2H, C$_6$H$_4$), 7.07 (d, J=8.7 Hz, 2H, C$_6$H$_4$), 8.73 (s, 1H, OH), 8.77 (s, 1H, OH). $^{13}$C NMR (acetone D$_6$): δ 35.1 (CH$_2$), 35.3 (CH$_2$), 35.8 (CH$_2$), 69.5 (2 CH C$_5$H$_4$), 70.6 (5CH Cp), 70.7 (2 CH C$_5$H$_4$), 89.2 (C C$_5$H$_4$), 116.5 (2 CH C$_6$H$_4$), 116.8 (2 CH C$_6$H$_4$), 132.0 (2 CH C$_6$H$_4$), 132.5 (2 CH C$_6$H$_4$), 134.6 (C), 137.6 (C), 138.0 (C), 140.8 (C), 157.6 (2 C). MS (EI, 70 eV) m/z: 516 [M]$^+$, 437, 371, 343, 286. HRMS (ESI, C$_{27}$H$_{25}$BrFeO$_2$: [M]$^+$) calcd: 516.0387. found: 516.0405.

2-ferrocenyl-1,1-bis-(4-hydroxyphenyl)-5-iodo-pent-1-ene, P615

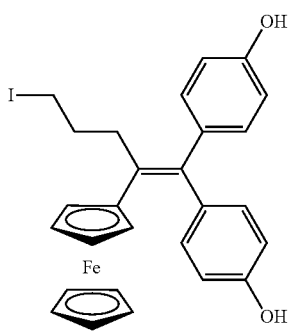

The brominated compound P528 was heated at reflux for three hours in technical grade acetone in the presence of 23 equivalents of potassium iodide. After concentration under reduced pressure, diethyl ether and water were added and the mixture was decanted. The aqueous layer was extracted and the combination of the organic layers was dried over magnesium sulphate and concentrated under reduced pressure to afford P615 in quantitative yield.

$^1$H NMR (acetone D$_6$): δ 1.95-2.06 (m, 2H, CH$_2$), 2.81 (t, J=8.0 Hz, 2H, CH$_2$), 3.21 (m, 3H, CH$_2$I), 4.01 (t, J=1.9 Hz, 2H, CH C$_5$H$_4$), 4.11 (t, J=1.9 Hz, 2H, CH C$_5$H$_4$), 4.18 (s, 5H, Cp), 6.75 (d, J=8.7 Hz, 2H, C$_6$H$_4$), 6.87 (d, J=8.7 Hz, 2H, C$_6$H$_4$), 6.90 (d, J=8.7 Hz, 2H, C$_6$H$_4$), 7.09 (d, J=8.7 Hz, 2H, C$_6$H$_4$), 8.30 (s, 1H, OH), 8.35 (s, 1H, OH). $^{13}$C NMR (acetone D$_6$): δ 30.9 (CH$_2$), 36.0 (CH$_2$), 37.4 (CH$_2$), 69.4 (2 CH C$_5$H$_4$), 70.5 (5CH Cp), 70.6 (2 CH C$_5$H$_4$), 89.2 (C C$_5$H$_4$), 116.5 (2 CH C$_6$H$_4$), 116.8 (2 CH C$_6$H$_4$), 131.9 (2 CH C$_6$H$_4$), 132.5 (2 CH C$_6$H$_4$), 134.3 (C), 137.5 (C), 137.9 (C), 140.8 (C), 157.5 (C). MS (EI, 70 eV) m/z: 564 [M]$^+$, 436 [M–HI]$^+$. HRMS (ESI, C$_{27}$H$_{25}$FeIO$_2$: [M]$^+$) calcd: 564.0249. found: 564.0236.

1.3. Preparation of Alcohol Derivatives

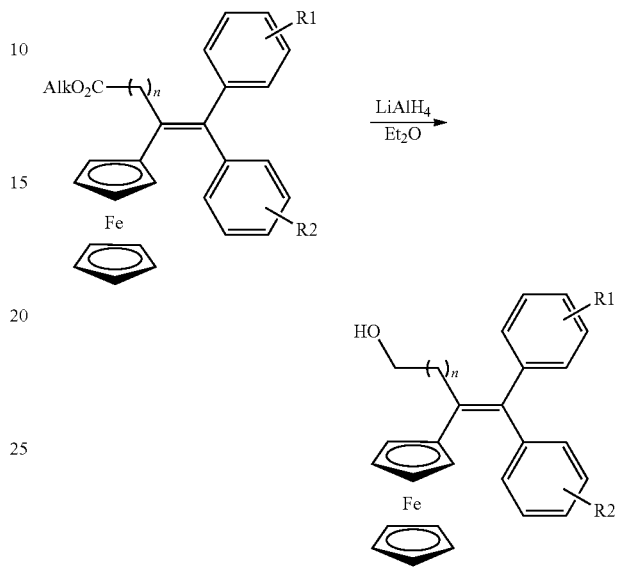

with Alk=(C$_1$-C$_6$)alkyl and n, R1 and R2 as defined above.

General Protocol (Reduction of the Ester Derivative):

In a flask containing diethyl ether was slowly added under stirring lithium aluminum hydride by portions. The corresponding ester, dissolved in dry THF, was slowly added, then the mixture was heated at reflux for 8 hours. The stirring was continued at room temperature overnight, then ethyl acetate was added dropwise, then ethanol, then water. The mixture was poured into a solution of sodium hydrogen carbonate and extracted twice with ether. The organic layer was washed with water, dried under magnesium sulfate, filtrated and concentrated under reduced pressure.

2-ferrocenyl-1,1-bis-(4-hydroxyphenyl)-4-hydroxy-but-1-ene, P110

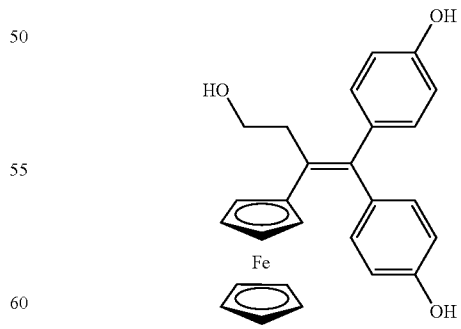

Yield: 71%. $^1$H NMR (acetone D$_6$): δ 2.98-3.08 (m, 2H, CH$_2$), 3.62-3.74 (m, 3H, CH$_2$O+OH), 4.08 (t, J=1.9 Hz, 2H, CH C$_5$H$_4$), 4.18 (t, J=1.9 Hz, 2H, CH C$_5$H$_4$), 4.25 (s, 5H, Cp), 6.80 (d, J=8.7 Hz, 2H, H$_{arom}$), 6.93 (d, J=8.7 Hz, 2H, H$_{arom}$), 6.96 (d, J=8.7 Hz, 2H, H$_{arom}$), 7.18 (d, J=8.7 Hz, 2H, H$_{arom}$), 8.33 (s, 1H, OH), 8.39 (s, 1H, OH). $^{13}$C NMR (acetone D$_6$): δ 39.5 (CH$_2$), 62.9 (CH$_2$O), 68.6 (2 CH C$_5$H$_4$), 69.8 (5CH Cp), 70.1 (2 CH C$_5$H$_4$), 88.8 (C C$_5$H$_4$), 115.7 (2 CH$_{arom}$), 115.9 (2 CH$_{arom}$), 131.2 (2 CH$_{arom}$), 131.8 (2 CH$_{arom}$), 137.0 (C), 137.3 (C), 140.6 (C), 145.8 (C), 156.7 (C), 156.8 (C). MS (EI, 70 eV) m/z: 440 [M]$^+$ 375 [M-Cp]$^+$ 121 [CpFe]$^+$. Anal. Calcd for C$_{26}$H$_{24}$FeO$_3$: C, 70.92; H, 5.49. Found: C, 70.64; H, 5.55.

2-ferrocenyl-1,1-bis-(4-hydroxyphenyl)-5-hydroxy-pent-1-ene, P53

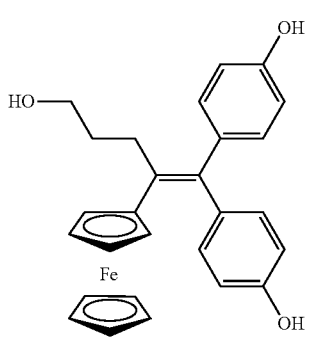

Yield: 82%. $^1$H NMR (acetone D$_6$): δ 1.72-1.85 (m, 2H, CH$_2$), 2.82 (t, J=8.0 Hz, 2H, CH$_2$), 3.51-3.60 (m, 3H, CH$_2$O+OH), 4.10 (t, J=1.9 Hz, 2H, CH C$_5$H$_4$), 4.17 (t, J=1.9 Hz, 2H, CH C$_5$H$_4$), 4.23 (s, 5H, Cp), 6.82 (d, J=8.7 Hz, 2H, C$_6$H$_4$), 6.93 (d, J=8.7 Hz, 2H, C$_6$H$_4$), 6.99 (d, J=8.7 Hz, 2H, C$_6$H$_4$), 7.18 (d, J=8.7 Hz, 2H, C$_6$H$_4$), 8.32 (s, 1H, OH), 8.35 (s, 1H, OH). $^{13}$C NMR (acetone D$_6$): δ 32.7 (CH$_2$), 35.6 (CH$_2$), 63.3 (CH$_2$O), 69.4 (2 CH C$_5$H$_4$), 70.6 (5CH Cp), 70.8 (2 CH C$_5$H$_4$), 89.3 (C C$_5$H$_4$), 116.5 (2 CH C$_6$H$_4$), 116.6 (2 CH C$_6$H$_4$), 132.0 (2 CH C$_6$H$_4$), 132.5 (2 CH C$_6$H$_4$), 136.0 (C), 138.0 (C), 138.3 (C), 139.9 (C), 157.3 (C), 157.4 (C). IR (KBr, ν cm$^{-1}$): 3433, 3519, 3560 (OH), 2887, 2955, 3222 (CH$_2$). MS (EI, 70 eV) m/z: 454 [M]$^+$, 389 [M-Cp]$^+$, 121 [FeCp]$^+$. HRMS (EI, 70 eV, C$_{27}$H$_{26}$FeO$_3$: [M]$^+$) calcd: 454.1232. found: 454.1237.

2-ferrocenyl-1,1-bis-(4-hydroxyphenyl)-6-hydroxy-hex-1-ene, P536

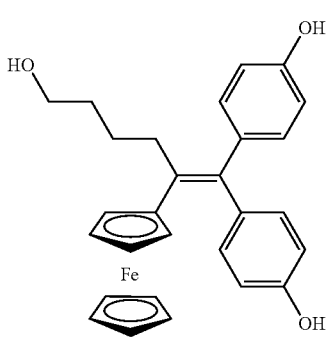

Yield: 100%. $^1$H NMR (acetone D$_6$): δ 1.24-1.36 (m, 2H, CH$_2$), 1.36-1.50 (m, 2H, CH$_2$), 2.52 (t, J=7.9 Hz, 2H, CH$_2$), 3.20-3.37 (m, 2H, CH$_2$O), 3.80 (t, J=1.9 Hz, 2H, CH C$_5$H$_4$), 3.92 (t, J=1.9 Hz, 2H, CH C$_5$H$_4$), 3.98 (s, 5H, Cp), 6.57 (d, J=8.6 Hz, 2H, H$_{arom}$), 6.67 (d, J=8.7 Hz, 2H, H$_{arom}$), 6.73 (d, J=8.6 Hz, 2H, H$_{arom}$), 6.92 (d, J=8.7 Hz, 2H, H$_{arom}$), 8.09 (s, 1H, OH), 8.12 (s, 1H, OH). $^{13}$C NMR (acetone D$_6$): δ 27.9 (CH$_2$), 33.8 (CH$_2$), 35.3 (CH$_2$), 62.3 (CH$_2$O), 68.6 (2 CH C$_5$H$_4$), 69.9 (5CH Cp), 70.1 (2 CH C$_5$H$_4$), 88.5 (C C$_5$H$_4$), 115.8 (2 CH$_{arom}$), 115.8 (2 CH$_{arom}$), 131.3 (2 CH$_{arom}$), 131.8 (2 CH$_{arom}$), 135.4 (C), 137.2 (C), 137.5 (C), 139.1 (C), 156.6 (C), 156.7 (CMS (CI, NH$_3$) m/z: 469 [M+H]'.

2-ferrocenyl-1,1-bis-(4-hydroxyphenyl)-7-hydroxy-hept-1-ene, P537

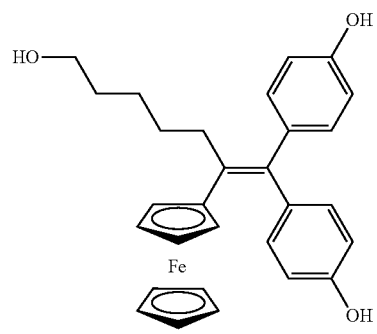

Yield: 100%. $^1$H NMR (acetone D$_6$): δ 1.09-1.22 (m, 2H, CH$_2$), 1.22-1.49 (m, 4H, 2CH), 2.50 (t, J=8.0 Hz, 2H, CH$_2$), 3.30-3.39 (m, 2H, CH$_2$), 3.78 (t, J=1.9 Hz, 2H, CH C$_5$H$_4$), 3.92 (t, J=1.9 Hz, 2H, CH C$_5$H$_4$), 3.98 (s, 5H, Cp), 6.57 (d, J=8.6 Hz, 2H, CH$_{arom}$), 6.67 (d, J=8.6 Hz, 2H, CH$_{arom}$), 6.73 (d, J=8.6 Hz, 2H, CH$_{arom}$), 6.92 (d, J=8.6 Hz, 2H, CH$_{arom}$), 8.08 (s, 1H, OH), 8.11 (s, 1H, OH). $^{13}$C NMR (acetone D$_6$): δ 26.9 (CH$_2$), 31.4 (CH$_2$), 33.6 (CH$_2$), 35.6 (CH$_2$), 62.5 (OCH$_2$), 68.6 (2CH C$_5$H$_4$), 69.9 (5CH Cp), 70.0 (2CH C$_5$H$_4$), 88.6 (C C$_5$H$_4$), 115.8 (2 CH$_{arom}$), 115.8 (2 CH$_{arom}$), 131.3 (2 CH$_{arom}$), 131.8 (2 CH$_{arom}$), 135.4 (C), 137.2 (C), 137.5 (C), 139.0 (C), 156.6 (C), 156.7 (C). MS (CI, NH$_3$) m/z: 483 [M+H]$^+$, 500 [M+NH$_4$]$^+$.

2-ferrocenyl-1-(4-hydroxyphenyl)-5-hydroxy-1-phenyl-pent-1-ene, P681

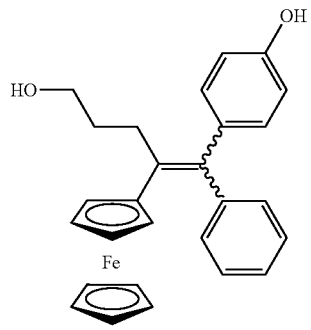

The reaction was done starting from the 50/50 mixture of Z and E isomers of P680. The isomers were separated by preparative HPLC (reverse phase with acetonitrile/water 80/20 as the eluent) but slowly converted into the 50/50 mixture.

Yield: 86%. $^1$H NMR (acetone D$_6$): δ 1.65-1.80 (m, 2H, CH$_2$), 2.65-2.80 (m, 2H, CH$_2$), 3.41-3.54 (m, 3H, CH$_2$O+OH), 3.97 and 4.05 (t, J=1.9 Hz, 2H, CH C$_5$H$_4$), 4.08 and 4.12 (t, J=1.9 Hz, 2H, CH C$_5$H$_4$), 4.16 and 4.17 (s, 5H, Cp), 6.77 and 6.86 (d, J=8.7 Hz, 2H, C$_6$H$_4$), 6.89-7.42 (m, 7H, H$_{arom}$), 8.32 and 8.34 (s, 1H, OH). $^{13}$C NMR (acetone D$_6$): δ 32.6 (CH$_2$), 35.6 (CH$_2$), 63.2 (CH$_2$O), 69.5 (2 CH C$_5$H$_4$), 70.7 (5 CH Cp), 70.9 (2 CH C$_5$H$_4$), 88.7 (C C$_5$H$_4$), 116.7 (2 CH C$_6$H$_4$), 127.6 (CH C$_6$H$_5$), 129.7 and 129.8 (2 CH$_{arom}$), 130.9 and 131.4 (2 CH$_{arom}$), 132.0 and 132.4 (2 CH$_{arom}$), 136.7 and 137.0 (C), 137.5 and 137.8 (C), 139.4 and 139.8 (C), 146.8 (C), 157.5 and 157.6 (C). MS (CI, N$_3$) m/z: 439 [M+H]$^+$. HRMS (ESI, C$_{27}$H$_{26}$FeO$_2$: [M]$^+$) calcd: 438.1282. found: 438.1288.

1,1-bis[4-(3-dimethylaminopropoxy)phenyl]-2-ferrocenyl-5-hydroxypent-1-ene, P651

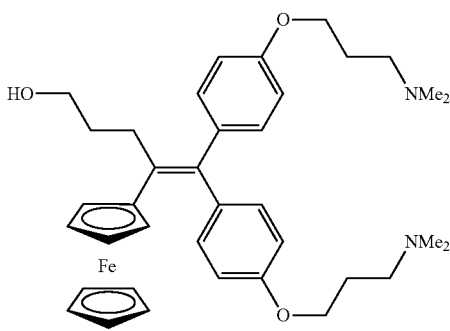

Yield: 96%. $^1$H NMR (CDCl$_3$): δ 1.61-1.75 (m, 2H, CH$_2$), 1.85-2.00 (m, 4H, 2 CH$_2$), 2.23 (s, 6H, NMe$_2$), 2.24 (s, 6H, NMe$_2$), 2.39-2.50 (m, 4H, 2 CH$_2$N), 2.69 (t, J=7.5 Hz, 2H, CH$_2$), 3.48 (t, J=6.4 Hz, 2H, CH$_2$O), 3.92 (t, J=1.9 Hz, 2H, CH C$_5$H$_4$), 3.93-4.02 (m, 4H, 2 CH$_2$O), 4.05 (t, J=1.9 Hz, 2H, CH C$_5$H$_4$), 4.10 (s, 5H, Cp), 6.72 (d, J=8.7 Hz, 2H, C$_6$H$_4$), 6.84 (d, J=8.7 Hz, 2H, C$_6$H$_4$), 6.92 (d, J=8.7 Hz, 2H, C$_6$H$_4$), 7.09 (d, J=8.7 Hz, 2H, C$_6$H$_4$). $^{13}$C NMR (CDCl$_3$): δ 27.8 (2 CH$_2$), 31.1 (CH$_2$), 34.0 (CH$_2$), 45.8 (2 NMe$_2$), 56.7 (2 CH$_2$N), 62.7 (CH$_2$OH), 66.3 (CH$_2$O), 66.4 (CH$_2$O), 68.4 (2 CH C$_5$H$_4$), 69.4 (5 CH Cp), 69.3 (2 CH C$_5$H$_4$), 87.7 (C C$_5$H$_4$), 114.4 (2 CH C$_6$H$_4$), 114.6 (2 CH C$_6$H$_4$), 130.9 (2 CH C$_6$H$_4$), 131.3 (2 CH C$_6$H$_4$), 134.6 (C), 137.3 (C), 137.6 (C), 138.3 (C), 157.6 (C), 157.7 (C). MS (EI, 70 eV) m/z: 624 [M]$^+$, 86 [(CH$_2$)$_3$NMe$_2$]$^+$, 58 [CH$_2$NMe$_2$]$^+$. HRMS (ESI, C$_{37}$H$_{48}$FeN$_2$O$_3$: [M]$^+$) calcd: 624.3014. found: 624.3004.

1,1-bis-(4-hydroxyphenyl)-5-hydroxy-2-ruthenocenyl-pent-1-en, W3

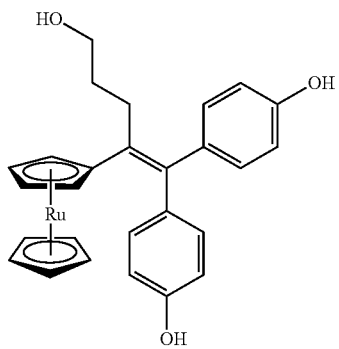

LiAlH$_4$ (0.12 g, 3.2 mmol) was added slowly to a solution of methyl 4-ene-5,5-bis-(4-hydroxyphenyl)-4-ruthenocenyl-pentanoate (W2) (0.3 g, 0.6 mmol) in 10 ml of THF. The mixture obtained was heated at reflux for 12 hrs. And then the reaction was quenched by water. The aqueous layer was extracted three times with EtOAc. The organic layer was dried over MgSO$_4$ and evaporated. The residue was purified by column chromatography on silica gel eluting with petroleum ether/ethyl acetate (2/1) to give 1,1-bis-(4-hydroxyphenyl)-5-hydroxy-2-ruthenocenyl-pent-1-en as a light yellow solid 0.2 g, yield 70%. $^1$H NMR (300 MHz, Acetone-d$_6$) δ 1.75 (m, 2H, CH$_2$), 2.53 (t, J=9.0 Hz, 2H, CH$_2$), 3.50 (q, J=6.3 Hz, 2H, OCH$_2$), 3.58 (t, J=6 Hz, 1H, OH), 4.45 (s, 4H, C$_5$H$_4$), 4.61 (s, 5H, C$_5$H$_5$), 6.77 (d, J=8.7 Hz, 2H, C$_6$H$_4$), 6.86 (d, J=8.6 Hz, 2H, C$_6$H$_4$), 6.96 (d, J=8.6 Hz, 2H, C$_6$H$_4$), 7.06 (d, J=8.6 Hz, 2H, C$_6$H$_4$), 8.36 (s, 1H, OH), 8.40 (s, 1H, OH); $^{13}$C NMR (75 MHz, Acetone-d$_6$) δ 33.4 (CH$_2$), 34.7 (CH$_2$), 62.6 (CH$_2$), 70.3 (2 CH C$_5$H$_4$), 71.8 (5 CH C$_5$H$_5$), 72.8 (2 CH C$_5$H$_4$), 93.9 (C C$_5$H$_4$), 115.6 (2 CH C$_6$H$_4$), 115.79 (2 CH C$_6$H$_4$), 131.2 (2 CH C$_6$H$_4$), 131.9 (2 CH C$_6$H$_4$), 134.1 (C C=C), 136.8 (C C=C), 137.2 (C C$_6$H$_4$), 139.3 (C C$_6$H$_4$), 156.6 (2 C C$_6$H$_4$); MS-EI m/z: 500 (M)$^+$.

1.4. Preparation of Acid Derivatives

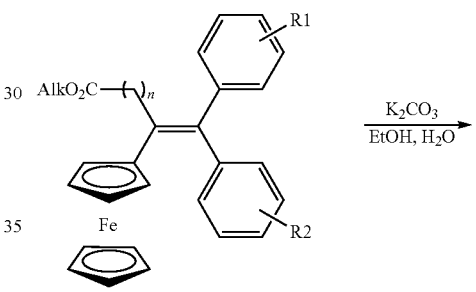

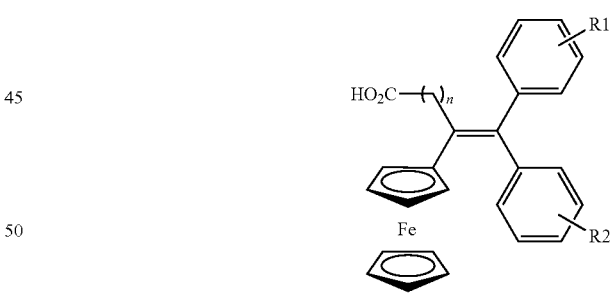

with Alk=(C$_1$-C$_6$)alkyl and n, R1 and R2 as defined above.

General Protocol (Saponification of the Ester Derivative):

Ester compound like P189 was heated for 1.5 hour in a solution of ethanol and water (35 mL and 10 mL for 1 mmol of P189 respectively) with 2 equivalents of potassium carbonate. After cooling, water and dichloromethane were added and after shaking the organic layer was discarded. The aqueous layer was acidified with hydrochloric acid and the precipitated P54 was extracted twice with dichloromethane. The combination of the organic layers was dried over magnesium sulphate, concentrated under reduced pressure to afford acid of type P54.

4-ene-4-ferrocenyl-5,5-bis-(4-hydroxyphenyl)-pentanoic acid, P54

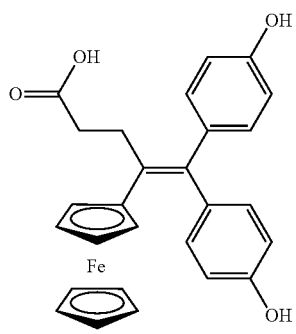

Yield: 96%. $^1$H NMR (acetone D$_6$): δ 2.46 (t, J=8.2 Hz, 2H, CH$_2$), 2.97 (t, J=8.2 Hz, 2H, CH$_2$), 3.03 (s broad, 1H, OH), 4.00 (t, J=1.9 Hz, 2H, C$_5$H$_4$), 4.13 (t, J=1.9 Hz, 2H, C$_5$H$_4$), 4.18 (s, 5H, Cp), 6.74 (d, J=8.7 Hz, 2H, C$_6$H$_4$), 6.86 (d, J=8.7 Hz, 2H, C$_6$H$_4$), 6.91 (d, J=8.7 Hz, 2H, C$_6$H$_4$), 7.12 (d, J=8.7 Hz, 2H, C$_6$H$_4$), 8.30 (s, 1H, OH), 8.35 (s, 1H, OH). $^{13}$C NMR (acetone D$_6$): δ 31.7 (CH$_2$), 35.8 (CH$_2$), 69.6 (2 CH C$_5$H$_4$), 70.6 (5 CH Cp), 70.7 (2 CH C$_5$H$_4$), 88.9 (C C$_5$H$_4$), 116.5 (2 CH C$_6$H$_4$), 116.8 (2 CH C$_6$H$_4$), 131.9 (2 CH C$_6$H$_4$), 132.5 (2 CH C$_6$H$_4$), 134.4 (C), 137.4 (C), 137.9 (C), 140.9 (C), 157.6 (2 C), 175.1 (CO). MS (CI, NH$_3$) m/z: 469 [M+H]$^+$, 485 [M+NH$_4$]$^+$.

1.5. Preparation of Amine, Amide and Imide Derivatives

Protocol of Preparation of Amino Compounds:

Halogenated compound like P687 was placed into a pressure tube and a solution of amine like dimethylamine in methanol (2 equivalent of amine) was added. The pressure tube was heated at 60° C. for 24 h, then was cooled to room temperature and concentrated under reduced pressure. The residue was chromatographed on a silica gel column with acetone, then acetone/triethylamine 10/1 as the eluents. After concentration under reduced pressure, the residue was crystallized from dichloromethane.

2-ferrocenyl-1,1-bis-(4-hydroxyphenyl)-5-dimethylamino-pent-1-ene, P697

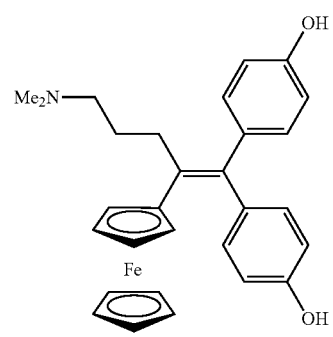

Yield: 36%. $^1$H NMR (DMSO D$_6$): δ 1.46-1.61 (m, 2H, CH$_2$), 2.02 (s, 6H, NMe$_2$), 2.12 (t, J=8.0 Hz, 2H, CH$_2$), 3.46-3.54 (m, 2H, CH$_2$N), 3.85 (t, J=1.9 Hz, 2H, CH C$_5$H$_4$), 4.11 (t, J=1.9 Hz, 2H, CH C$_5$H$_4$), 4.14 (s, 5H, Cp), 6.65 (d, J=8.7 Hz, 2H, C$_6$H$_4$), 6.74 (d, J=8.7 Hz, 2H, C$_6$H$_4$), 6.81 (d, J=8.7 Hz, 2H, C$_6$H$_4$), 7.00 (d, J=8.7 Hz, 2H, C$_6$H$_4$), 9.33 (s broad, 2H, OH). $^{13}$C NMR (DMSO D$_6$): δ 29.1 (CH2), 32.9 (CH2), 45.9 (NMe2), 60.1 (CH2N), 68.7 (2 CH C5H4), 69.6 (2 CH C5H4), 69.9 (5CH Cp), 87.9 (C C5H4), 116.0 (2×2 CH C6H4), 130.9 (2 CH C6H4), 131.3 (2 CH C6H4), 134.7 (C), 136.3 (C), 136.6 (C), 138.8 (C), 156.5 (C), 156.6 (C). MS (CI, NH$_3$) m/z: 482 [M+H]$^+$. HRMS (ESI, C$_{29}$H$_{31}$FeNO$_2$: [M]$^+$) calcd: 481.1704. found: 481.1689.

Protocol of Preparation of Imide Compounds:

Chlorinated compound like P687 was heated overnight with a mixture of potassium carbonate (2 equivalents), phthalimide (2 equivalents) and DMF (10 mL/mmol of P687). After cooling, the mixture was poured into water containing 2 equivalents of sodium hydroxide, and diethyl ether. Then the mixture was shaked and decanted. The aqueous layer was extracted with diethyl ether. The combination of organic layers was dried over magnesium sulphate, concentrated under reduced pressure, and chromatographed on a silica gel column with a mixture of cyclohexane/ethyl acetate as the eluent to afford the imide.

N-{4-ferrocenyl-5,5-bis-(4-hydroxyphenyl)-pent-4-enyl}phthalimide, P686

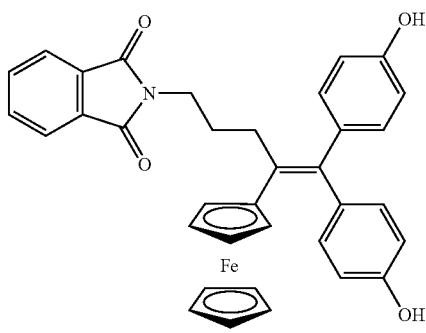

Yield: 83%. $^1$H NMR (acetone D$_6$): δ 1.83-1.97 (m, 2H, CH$_2$), 2.71 (t, J=8.3 Hz, 2H, CH$_2$), 3.62 (t, J=6.8 Hz, 2H, CH$_2$N), 3.92 (t, J=1.9 Hz, 2H, CH C$_5$H$_4$), 4.07 (t, J=1.9 Hz, 2H, CH C$_5$H$_4$), 4.10 (s, 5H, Cp), 6.70 (d, J=8.7 Hz, 2H, H$_{arom}$), 6.72 (d, J=8.7 Hz, 2H, H$_{arom}$), 6.89 (d, J=8.7 Hz, 2H, H$_{arom}$), 7.02 (d, J=8.7 Hz, 2H, H$_{arom}$), 7.88 (s, 4H, phthalimide), 8.14 (s, 1H, OH), 8.26 (s, 1H, OH). $^{13}$C NMR (acetone D$_6$): δ 30.6 (CH$_2$), 33.8 (CH$_2$), 39.2 (CH$_2$), 69.4 (2 CH C$_5$H$_4$), 70.6 (5CH Cp), 70.7 (2 CH C$_5$H$_4$), 89.1 (C C$_5$H$_4$), 116.4 (2 CH C$_6$H$_4$), 116.5 (2 CH C$_6$H$_4$), 124.4 (2 CH phthalimide), 131.8 (2 CH C$_6$H$_4$), 132.5 (2 CH C$_6$H$_4$), 133.8 (2 C phthalimide), 135.0 (C), 135.7 (2 CH phthalimide), 137.4 (C), 138.0 (C), 138.3 (C), 140.5 (C), 157.4 (C), 157.5 (C), 169.6 (2 CO). IR (KBr, ν cm$^{-1}$): 3429 (OH), 3085, 2944, 2874 (CH, CH$_2$), 1700 (CO). MS (CI, NH$_3$) m/z: 584 [M+H]$^+$, 601 [M+NH$_4$]$^+$. HRMS (ESI, C$_{35}$H$_{29}$FeNO$_4$: [M]$^+$) calcd: 583.1446. found: 583.1466.

N-{5-ferrocenyl-6,6-bis-(4-hydroxyphenyl)-hex-5-enyl}phthalimide, P720

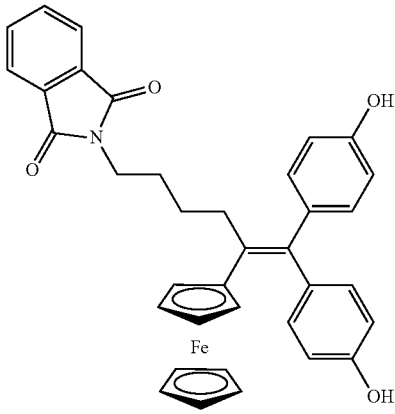

Yield: 94%. $^1$H NMR (acetone D$_6$): δ 1.50-1.73 (m, 4H, CH$_2$—CH$_2$), 2.72 (t, J=7.6 Hz, 2H, CH$_2$—C=C), 3.60 (t, J=6.9 Hz, 2H, CH$_2$N), 3.94 (t, J=1.9 Hz, 2H, H C$_5$H$_4$), 4.07 (t, J=1.9 Hz, 2H, H C$_5$H$_4$), 4.15 (s, 5H, H Cp), 6.72 (d, J=8.5 Hz, 2H, H C$_6$H$_4$), 6.73 (d, J=8.5 Hz, 2H, H C$_6$H$_4$), 6.72 (d, J=8.5 Hz, 2H, H C$_6$H$_4$), 6.87 (d, J=8.5 Hz, 2H, H C$_6$H$_4$), 7.02 (d, J=8.5 Hz, 2H, H C$_6$H$_4$), 7.88 (s, 4H, Hphth), 8.27 (s, 1H, OH), 8.28 (s, 1H, OH). $^{13}$C NMR (acetone D$_6$): δ 28.2 (CH$_2$), 28.9 (CH$_2$), 34.6 (CH$_2$), 38.0 (CH$_2$), 68.3 (2 CH C$_5$H$_4$), 69.5 (5 CH Cp), 69.7 (2 CH C$_5$H$_4$), 88.2 (C C$_5$H$_4$), 115.4 (2 CH C$_6$H$_4$), 115.5 (2 CH C$_6$H$_4$), 123.3 (2 CHphth), 130.9 (2 CH C$_6$H$_4$), 131.4 (2 CH C$_6$H$_4$), 132.8 (2 C), 134.6 (2 CHphth+C), 136.7 (C), 137.1 (C), 139.1 (C), 156.3 (C), 156.4 (C), 168.4 (2 CO). IR (KBr, ν cm$^{-1}$): 3431 (OH), 3096, 3028, 2939 (CH, CH$_2$), 1700 (CO). MS (EI, 70 eV) m/z: 597 [M]$^+$ 532 [M-Cp]$^+$, 382, 343. HRMS (ESI, C$_{36}$H$_3$, FeNO$_4$: [M]$^+$) calcd: 597.1602. found: 597.1617.

N-{4-ferrocenyl-5,5-bis-(4-hydroxyphenyl)-pent-4-enyl}succinimide, P722

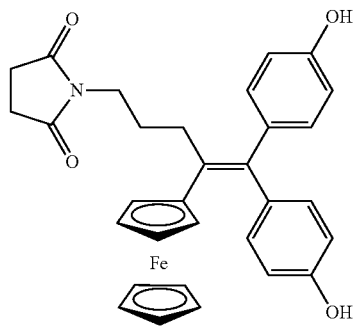

Yield: 54%. $^1$H NMR (acetone D$_6$): δ 1.70-1.81 (m, 2H, CH$_2$), 2.56-2.64 (m, 6H, 2 CH$_2$ succ+CH$_2$—C=C), 3.38 (t, J=6.6 Hz, 2H, CH$_2$N), 3.95 (t, J=1.9 Hz, 2H, H C$_5$H$_4$), 4.10 (t, J=1.9 Hz, 2H, H C$_5$H$_4$), 4.16 (s, 5H, H Cp), 6.74 (d, J=8.6 Hz, 2H, H C$_6$H$_4$), 6.85 (d, J=8.6 Hz, 2H, H C$_6$H$_4$), 6.91 (d, J=8.6 Hz, 2H, H C$_6$H$_4$), 7.04 (d, J=8.6 Hz, 2H, H C$_6$H$_4$), 8.25 (s, 1H, OH), 8.36 (s, 1H, OH). $^{13}$C NMR (acetone D$_6$): δ 29.4 (2 CH$_2$ succ), 30.8 (CH$_2$), 33.8 (CH$_2$), 39.7 (CH$_2$), 69.5 (2 CH C$_5$H$_4$), 70.7 (5 CH Cp+2 CH C$_5$H$_4$), 88.8 (C C$_5$H$_4$), 116.5 (2 CH C$_6$H$_4$), 116.6 (2 CH C$_6$H$_4$), 132.0 (2 CH C$_6$H$_4$), 132.4 (2 CH C$_6$H$_4$), 135.3 (C), 137.7 (C), 137.9 (C), 140.2 (C), 157.3 (C), 157.5 (C), 178.6 (2 CO). IR (KBr, ν cm$^{-1}$): 3421 (OH), 3096, 2967, 2936 (CH, CH$_2$), 1697 (CO). MS (ESI) m/z: 535 [M]$^+$, 342, 279, 224, 143, 83. HRMS (ESI, C$_{31}$H$_{29}$FeNO$_4$: [M]$^+$) calcd: 535.1446. found: 535.1460.

N-{5-ferrocenyl-6,6-bis-(4-hydroxyphenyl)-hex-5-enyl}succinimide, P723

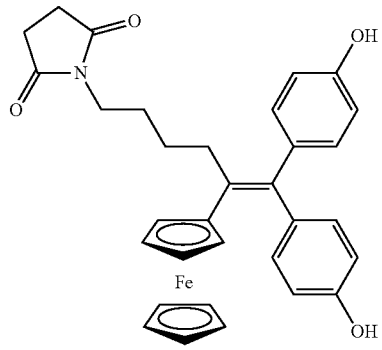

Yield: 58%. $^1$H NMR (acetone D$_6$): δ 1.42-1.54 (m, 4H, CH$_2$—CH$_2$), 2.66-2.71 (m, 6H, 2 CH$_2$ succ+CH$_2$—C=C), 3.35 (t, J=6.6 Hz, 2H, CH$_2$N), 3.95 (t, J=1.9 Hz, 2H, H C$_5$H$_4$), 4.10 (t, J=1.9 Hz, 2H, H C$_5$H$_4$), 4.17 (s, 5H, HCp), 6.73 (d, J=8.6 Hz, 2H, H C$_6$H$_4$), 6.84 (d, J=8.6 Hz, 2H, H C$_6$H$_4$), 6.89 (d, J=8.6 Hz, 2H, H C$_6$H$_4$), 7.08 (d, J=8.6 Hz, 2H, H C$_6$H$_4$), 8.25 (s, 1H, OH), 8.30 (s, 1H, OH). $^{13}$C NMR (acetone D$_6$): δ 28.1 (2 CH$_2$), 28.3 (2 CH$_2$), 34.6 (CH$_2$), 38.4 (CH$_2$), 68.3 (2 CH C$_5$H$_4$), 69.5 (5 CH Cp), 69.7 (2 CH C$_5$H$_4$), 88.2 (C C$_5$H$_4$), 115.4 (2 CH C$_6$H$_4$), 115.5 (2 CH C$_6$H$_4$), 130.9 (2 CH C$_6$H$_4$), 131.4 (2 CH C$_6$H$_4$), 134.6 (C), 136.7 (C), 137.0 (C), 139.0 (C), 156.3 (C), 156.4 (C), 177.7 (2 CO). IR (KBr, ν cm$^{-1}$): 3393 (OH), 3096, 3023, 2940, 2879 (CH, CH$_2$), 1681 (CO). MS (EI, 70 eV) m/z: 549 [M]$^+$., 484 [M-Cp]$^+$, 442, 382, 343, 286, 186.

1.6. Preparation of Hydroxyamide and Alkoxyamide Derivatives

Protocol:

Imide like P686 was dissolved into methanol at 5-15° C., then sodium borohydride was added portionwise until all imide has disappeared (controlled by TLC). The mixture was poured into a solution of sodium hydrogenocarbonate in water and the mixture was extracted with dichloromethane twice. The combination of the organic layers was dried over magnesium sulpate, then concentrated under reduced pressure to afford the hydroxyamide.

If hydrochloric acid was added to the mixture containing P721, and the mixture was poured into water, in place of pouring the mixture directly into a solution of sodium hydrogenocarbonate in water, only the methoxy compound P727 was obtained.

2,3-Dihydro-3-hydroxy-2-[4-ferrocenyl-5,5-bis-(4-hydroxyphenyl)-pent-4-enyl]-1H-isoindol-1-one, P710

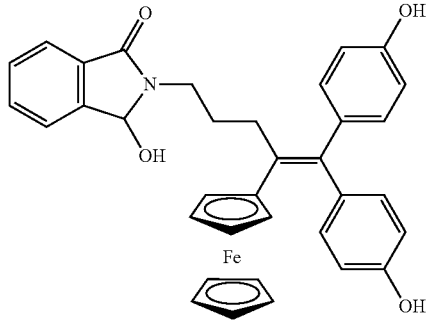

Yield: 92%. $^1$H NMR (acetone $D_6$): δ 1.85-1.98 (m, 2H, $CH_2$), 2.62-2.83 (m, 2H, $CH_2$—C=C), 3.29-3.38 (m, 1H, $CH_2N$), 3.67-3.81 (m, 1H, $CH_2N$), 3.82-3.86 (m, 1H, H $C_5H_4$), 4.03-4.06 (m, 1H, H $C_5H_4$), 4.06-4.15 (m, 7H, H Cp+H $C_5H_4$), 5.35 (d, J=4.7 Hz, 1H, OH), 5.53 (d, J=4.7 Hz, 1H, CH), 6.72 (d, J=8.6 Hz, 2H, H $C_6H_4$), 6.75 (d, J=8.6 Hz, 2H, H $C_6H_4$), 6.89 (d, J=8.6 Hz, 2H, H $C_6H_4$), 7.06 (d, J=8.6 Hz, 2H, H $C_6H_4$), 7.53-7.71 (m, 4H, H phth), 8.28 (s, 1H, OH), 8.29 (s, 1H, OH). $^{13}$C NMR (acetone $D_6$): δ 29.3 ($CH_2$), 32.9 ($CH_2$), 39.1 ($CH_2$), 68.3 (CH $C_5H_4$), 68.4 (CH $C_5H_4$), 69.6 (5 CH Cp+1 CH $C_5H_4$), 69.8 (CH $C_5H_4$), 81.2 (CH—OH), 88.2 (C $C_5H_4$), 115.5 (2 CH $C_6H_4$), 115.6 (2 CH $C_6H_4$), 122.9 (CH phth), 124.0 (CH phth), 129.8 (CH phth), 131.0 (2 CH $C_6H_4$), 131.5 (2 CH $C_6H_4$), 132.2 (CH phth), 134.4 (C), 136.6 (C), 137.0 (C), 139.0 (2 C), 145.6 (C), 156.7 (C), 156.8 (C), 167.2 (CO). IR (KBr, ν $cm^{-1}$): 3406 (OH), 2956, 2927, 2868 (CH, $CH_2$), 1665 (CO). MS (EI, 70 eV) m/z: 585 [M]$^+$, 520 [M-Cp]$^+$, 502 [M-Cp-$H_2O$]$^+$, 474, 369, 341, 146. HRMS (ESI, $C_{35}H_{31}FeNO_4$: [M]$^+$) calcd: 585.1602. found: 585.1623.

2,3-Dihydro-3-hydroxy-2[5-ferrocenyl-6,6-bis-(4-hydroxyphenyl)-hex-5-enyl]-1H-isoindol-1-one, P721

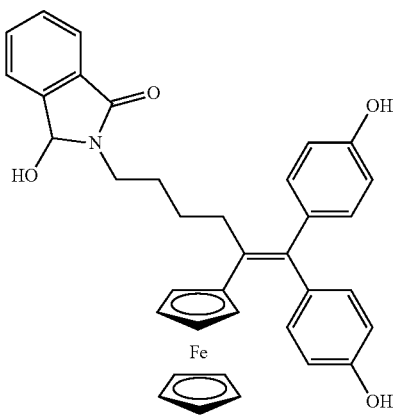

Yield: 72%. $^1$H NMR (acetone $D_6$): δ 1.52-1.75 (m, 4H, $CH_2$—$CH_2$), 2.74 (t, J=7.6 Hz, 2H, $CH_2$—C=C), 3.31-3.40 (m, 1H, $CH_2N$), 3.64-3.65 (m, 1H, $CH_2N$), 3.90-3.95 (m, 1H, H $C_5H_4$), 3.95-4.00 (m, 1H, H $C_5H_4$), 4.03-4.09 (m, 2H, H $C_5H_4$), 4.16 (s, 5H, H Cp), 5.47 (d, J=4.7 Hz, 1H, OH), 5.87 (d, J=4.7 Hz, 1H, CH), 6.73 (d, J=8.5 Hz, 2H, H $C_6H_4$), 6.79 (d, J=8.5 Hz, 2H, H $C_6H_4$), 6.89 (d, J=8.5 Hz, 2H, H $C_6H_4$), 7.06 (d, J=8.5 Hz, 2H, H $C_6H_4$), 7.53-7.72 (m, 4H, H phth), 8.31 (s, 1H, OH), 8.34 (s, 1H, OH). $^{13}$C NMR (acetone $D_6$): δ 28.8 ($CH_2$), 29.0 ($CH_2$), 34.9 ($CH_2$), 39.1 ($CH_2$), 68.3 (2 CH $C_5H_4$), 69.5 (5 CH Cp), 69.7 (2 CH $C_5H_4$), 81.6 (CH—OH), 88.1 (C $C_5H_4$), 115.4 (2 CH $C_6H_4$), 115.5 (2 CH $C_6H_4$), 122.9 (CH phth), 123.9 (CH phth), 129.8 (CH phth), 130.9 (2 CH $C_6H_4$), 131.4 (2 CH $C_6H_4$), 132.2 (CH phth), 132.9 (C), 134.8 (C), 136.8 (C), 137.1 (C), 138.9 (C), 145.5 (C), 156.3 (C), 156.4 (C), 166.8 (CO). IR (KBr, ν $cm^{-1}$): 3434 (OH), 3023, 2933, 2858 (CH, $CH_2$), 1672 (CO). MS (EI, 70 eV) m/z: 599 [M]$^+$, 534 [M-Cp]$^+$, 516 [M-Cp-$H_2O$]$^+$, 490, 383, 343. HRMS (ESI, $C_{36}H_{33}FeNO_4$: [M]$^+$) calcd: 599.1759. found: 599.1775.

2,3-Dihydro-3-methoxy-2-[5-ferrocenyl-6,6-bis-(4-hydroxyphenyl)-hex-5-enyl]-1H-isoindol-1-one, P727

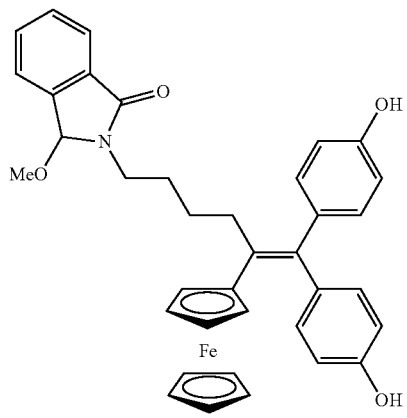

Yield: 67%. $^1$H NMR (acetone $D_6$): δ 1.52-1.68 (m, 4H, 2 $CH_2$); 2.74 (t, J=7.6 Hz, 2H, $CH_2$C=C); 2.91 (s, 3H, $CH_3$), 3.09-3.23 (m, 1H, $CH_2N$); 3.61-3.74 (m, 1H, $CH_2N$); 3.91-3.95 (m, 1H, Hcp); 3.95-3.99 (m, 1H, Hcp); 4.04-4.10 (m, 2H, Hcp); 4.16 (s, 5H, H Cp); 5.87 (s, 1H, CH); 6.72 (d, J=8.6 Hz, 2H, $C_6H_4$); 6.78 (d, J=8.6 Hz, 2H, $C_6H_4$); 6.89 (d, J=8.6 Hz, 2H, $C_6H_4$); 7.05 (d, J=8.6 Hz, 2H, $C_6H_4$); 7.59-7.78 (m, 4H, Hphth); 8.23 (s, 1H, OH); 8.26 (s, 1H, OH). $^{13}$C NMR (acetone $D_6$): δ 27.2 ($CH_2$); 28.5 ($CH_2$); 34.8 ($CH_2$); 39.6 ($CH_2$); 49.4 ($OCH_3$); 68.3 (2 CH $C_5H_4$); 69.5 (5 CH CO; 69.7 (2 CH $C_5H_4$); 86.7 (CH-0); 88.1 (C $C_5H_4$); 115.4 (2 CH $C_6H_4$); 115.5 (2 CH $C_6H_4$); 123.2 (CHphth); 124.1 (CHphth); 130.3 (CHphth); 130.9 (2 CH $C_6H_4$); 131.4 (2 CH $C_6H_4$); 132.4 (CHphth); 133.8 (C); 134.8 (C); 136.7 (C); 137.0 (C); 138.9 (C); 141.5 (C); 156.2 (C); 156.3 (C); 167.2 (CO). IR (KBr, ν $cm^{-1}$): 3419 (OH), 3091, 3019, 2934, 2868 (CH, $CH_2$), 1680 (CO). MS (EI, 70 eV) m/z: 613 [M]$^+$, 548 [M-Cp]$^+$, 516 [M-Cp-MeOH]$^+$, 343. HRMS (ESI, $C_{37}H_{35}FeNO_4$: [M]$^+$) calcd: 613.1915. found: 613.1943.

Example 2: Antiproliferative Effects of Compounds of the Invention on Various Cancer Cell Lines The antiproliferative effects of compounds of the invention were tested on MDA-MB-231 cells (non-hormone-dependent breast cancer cells), on PC3 cells (non-hormonedependent prostate cancer cells), on Mia-PaCa cells (pancreatic cancer cells) and on HepG2 cells (hepatocellular liver carcinoma cells) as described below.

Cell Culture and Cell Proliferation Assay.

The cell lines MDA-MB-231 and PC3 were obtained from ATCC, and the cell lines Mia-PaCa and HepG2 were obtained from ACACC. Cells were grown in RPMI medium supplemented with 10% fetal calf serum, in the presence of penicillin, streptomycin, and fungizone in a 75 cm² flask under 5% $CO_2$. Cells were plated in 96-well tissue culture plates in 200 µL of medium and treated 24 h later with 2 µL stock solutions of compounds dissolved in DMSO using a Biomek 3000 instrument (Beckman-Coulter). Controls received the same volume of DMSO (1% final volume). After 72 h of exposure, MTS reagent (Promega) was added and incubated for 3 h at 37° C.: the absorbance was monitored at 490 nm and results expressed as the inhibition of cell proliferation calculated as the ratio (1−(OD490 treated/OD490 control))×100 in triplicate experiments. For $IC_{50}$ determination (50% inhibition of cell proliferation), cells were incubated for 72 h following the same protocol with compound concentrations ranging from 5 nM to 100 µM in separate duplicate experiments.

Results.

The results obtained are shown in Tables 1 and 2 below and demonstrate the antiproliferative properties of the compounds of the invention on various cancer cell lines.

TABLE 1

| Tested compounds | $IC_{50}$ (µM) MDA-MB-231 |
| --- | --- |
| P110 | 0.36 |
| P53 | 0.065 |
| P536 | 0.17 |
| P537 | 0.28 |
| P681 | 1.22 |
| P64 | 1.16 |
| P189 | 0.36 |
| P49 | 0.58 |
| P188 | 0.24 |
| P504 | 0.62 |
| P686 | 0.20 |
| P697 | 2.53 |
| P720 | 0.33 |
| P722 | 0.86 |
| P710 | 0.59 |
| P721 | 0.12 |
| P727 | 1.63 |
| W3 | 12.45 |

TABLE 2

| Cancer cell line | $IC_{50}$ (µM) of P53 |
| --- | --- |
| MDA-MB-231 | 0.065 |
| PC3 | 4.43 |
| Mia-PaCa | 1.23 |
| HepG2 | 0.07 |

A comparative study on the MDA-MB-231 cell line comparing the compounds of the invention and the unsubstituted analogs showed that the compounds of the invention display a greater cytotoxic activity than the unsubstituted analogs, as shown in Table 3 below.

TABLE 3

| Compound of the invention | Unsubstituted analog |
| --- | --- |
| 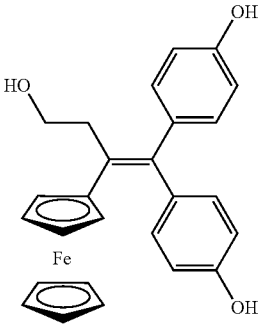 $IC_{50} = 0.36 \pm 0.06$ µM | 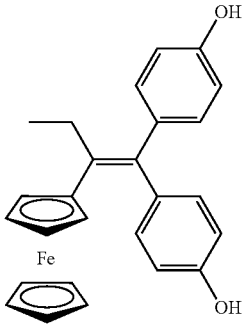 $IC_{50} = 0.64 \pm 0.06$ µM |
| 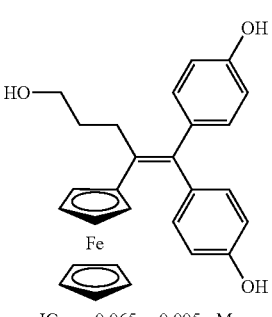 $IC_{50} = 0.065 \pm 0.005$ µM | 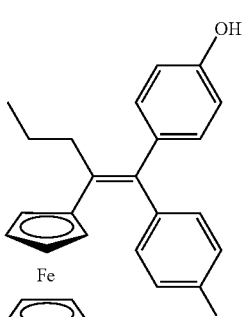 $IC_{50} = 2.06 \pm 0.14$ µM |
| 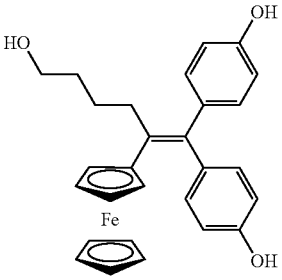 $IC_{50} = 0.17 \pm 0.05$ µM | 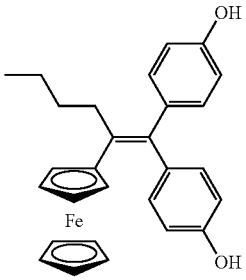 $IC_{50} = 3.23 \pm 0.17$ µM |
| 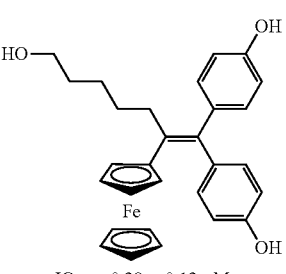 $IC_{50} = 0.28 \pm 0.12$ µM | 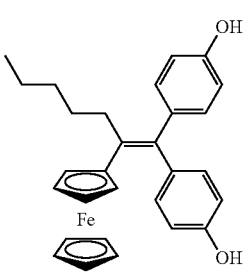 $IC_{50} = 3.75 \pm 0.21$ µM |

A comparative study on the MDA-MB-231 cell line comparing compounds of the invention and chlorinated analogs showed that the compounds of the invention display a greater cytotoxic activity than the chlorinated analogs, as shown in Table 4 below.

TABLE 4

| Compound of the invention | Chlorinated analog |
|---|---|
| (structure with HO-CH2CH2- group, Fe, two 4-OH-phenyl groups)<br>$IC_{50} = 0.36 \pm 0.06$ μM | (structure with Cl-CH2CH2- group, Fe, two 4-OH-phenyl groups)<br>$IC_{50} = 1.00 \pm 0.10$ μM |
| (structure with HO-(CH2)3- group, Fe, two 4-OH-phenyl groups)<br>$IC_{50} = 0.065 \pm 0.005$ μM | (structure with Cl-(CH2)3- group, Fe, two 4-OH-phenyl groups)<br>$IC_{50} = 4.63 \pm 0.44$ μM |

The invention claimed is:

1. A compound of the following formula (I):

(I)

or a pharmaceutically acceptable salt or solvate thereof, a stereoisomer or a mixture of stereoisomers in any ratio, or a water-soluble derivative,
in which:
M is Fe, Ru or Os,
n is an integer comprised between 1 and 8,
R1 and R2 are, independently from each other, H, $CF_3$, CN, $OR^4$ or $NR^5R^6$, and
R3 is $CO_2R^7$, $OR^8$ or $NR^9R^{10}$,
wherein:
$R^4$ is H, $(C_1\text{-}C_6)$alkyl, —CO—$(C_1\text{-}C_6)$alkyl or —$(CH_2)_m$ $NR^{11}R^{12}$,
$R^5$, $R^6$, $R^{11}$ and $R^{12}$ are, independently from one another, H, $(C_1\text{-}C_6)$alkyl or —CO—$(C_1\text{-}C_6)$alkyl,
$R^7$ is H or $(C_1\text{-}C_6)$alkyl,
$R^8$ is H, $(C_1\text{-}C_6)$alkyl or —CO—$(C_1\text{-}C_6)$alkyl,
$R^9$ and $R^{10}$ are, independently from one another, H, $(C_1\text{-}C_6)$alkyl or —CO—$(C_1\text{-}C_6)$alkyl, or $R^9$ and $R^{10}$ form together with the nitrogen atom bearing them a cycle of the following formula:

in which:
===== represents a single or double bond,
X1 and X2 are, independently from one another, C=O, $SO_2$, CH—$OR^{19}$, CH—$SR^{20}$, CH—$NR^{21}R^{22}$ or CH—NHC(O)$R^{23}$,
$R^{13}$ and $R^{14}$ are, independently from one another, H or $(C_1\text{-}C_6)$alkyl, or
$R^{13}$ and $R^{14}$ form together with the carbon atoms bearing them a 5- or 6-membered hydrocarbon cycle,
$R^{19}$, $R^{20}$, $R^{21}$ and $R^{22}$ are, independently from one another, H or $(C_1\text{-}C_6)$alkyl, and
$R^{23}$ is a $(C_1\text{-}C_6)$alkyl group, and
m is an integer comprised between 1 and 8.

2. The compound according to claim 1, wherein n is an integer comprised between 2 and 6.

3. The compound according to claim 1, wherein it has the following formula (Ia):

(Ia)

4. The compound according to claim 1, wherein M is Fe.

5. The compound according to claim 1, wherein R1 and R2 are, independently from each other, H, $OR^4$ or $NR^5R^6$.

6. The compound according to claim 1, wherein one of R1 and R2 is $OR^4$ and the other is H or $OR^4$.

7. The compound according to claim 1, wherein R3 is $CO_2R^7$, $OR^8$ or $NR^9R^{10}$ with:
$R^7$ being a —$(C_1\text{-}C_6)$alkyl group,
$R^8$ being H, and
at least one of $R^9$ and $R^{10}$ being, independently from one another, —CO—$(C_1\text{-}C_6)$alkyl, or $R^9$ and $R^{10}$ forming together with the nitrogen atom bearing them a cycle of the following formula:

in which =====, $R^{13}$ and $R^{14}$ are as defined in claim 1, and at least one of X1 and X2 is C=O.

8. The compound according to claim 1, selected from the following compounds:
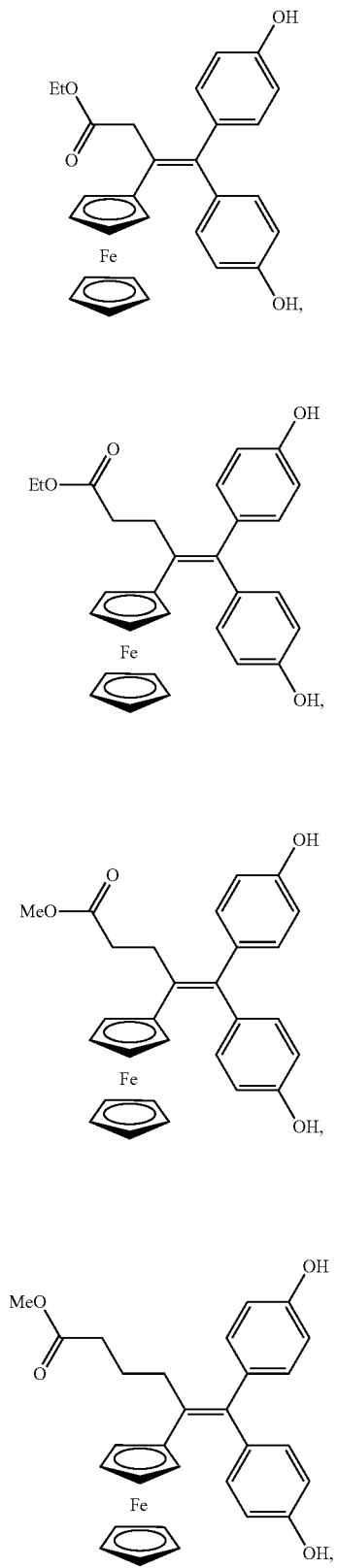
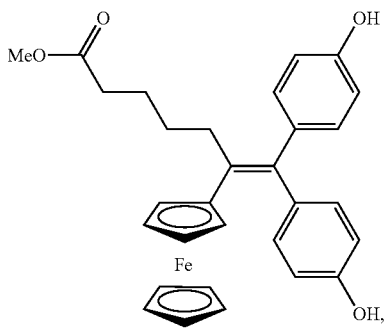
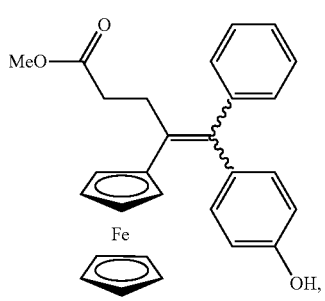
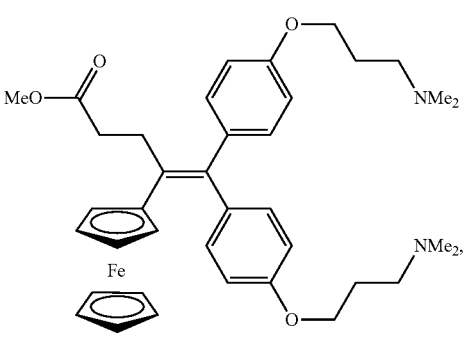
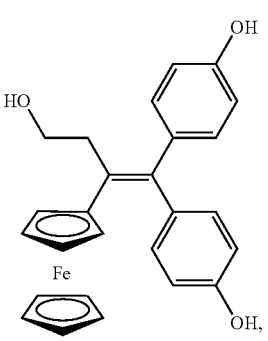
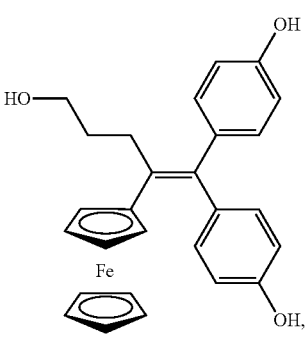

-continued
P536
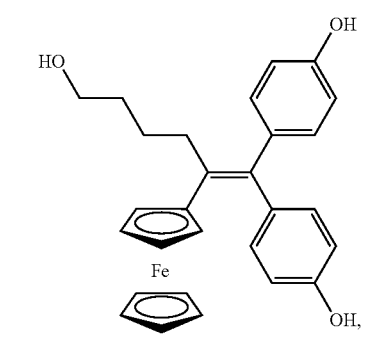
P537
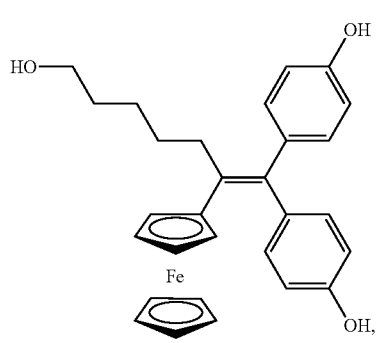
P681
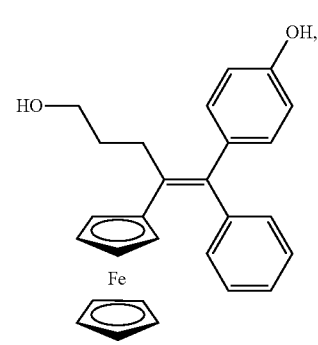
P651
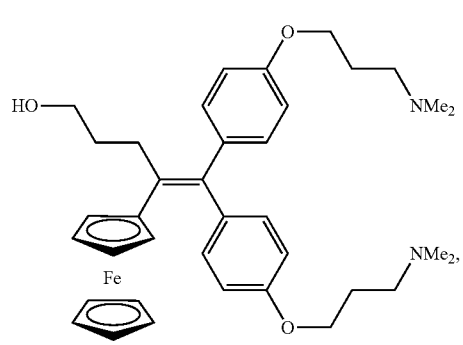
P54
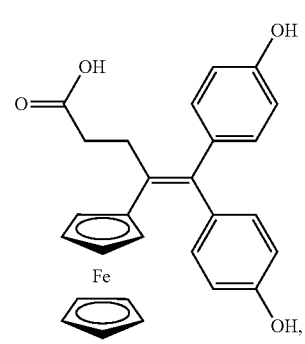
-continued
P697
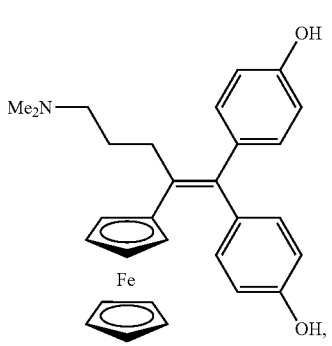
P686
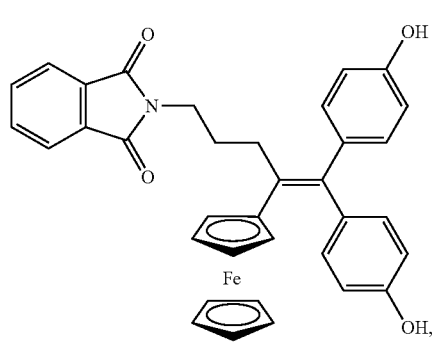
P720
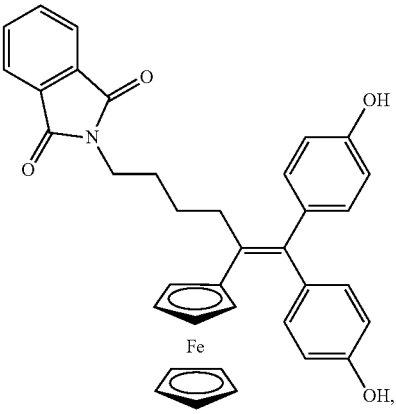
P722
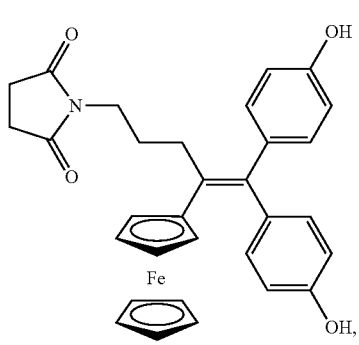

P723

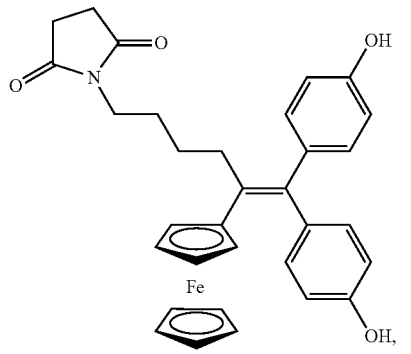

P710

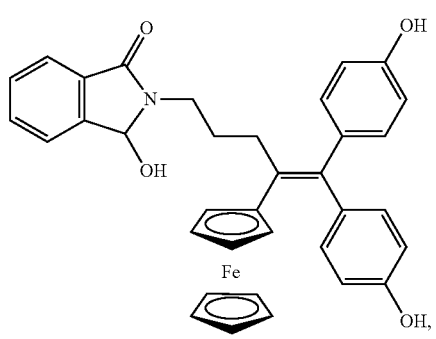

P721

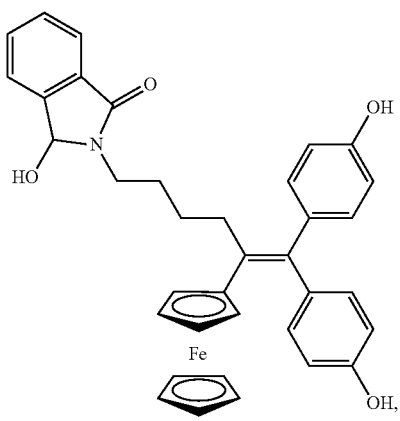

P727

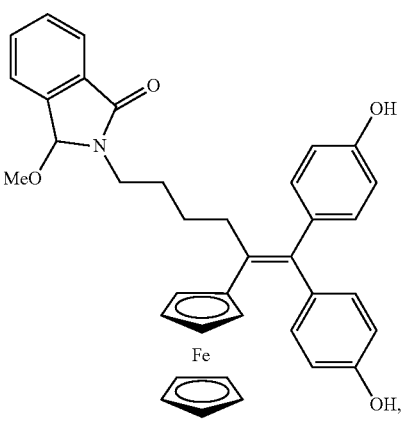

W2

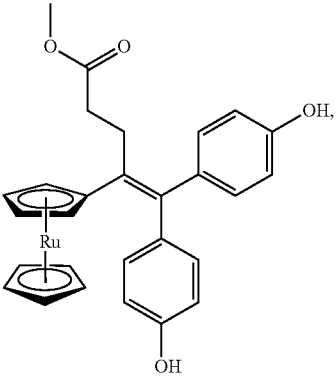

W3

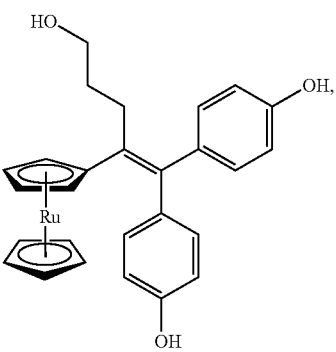

and pharmaceutically acceptable salts and solvates thereof.

9. A pharmaceutical composition comprising at least one compound according to claim 1, in combination with at least one pharmaceutically acceptable vehicle.

10. The pharmaceutical composition according to claim 9, further comprising at least one additional active ingredient.

11. The pharmaceutical composition according to claim 10, wherein the at least one additional active ingredient is selected from 6-mercaptopurin, fludarabin, cladribin, pentostatin, cytarabin, 5-fluorouracil, gemcitabin, methotrexate, raltitrexed, irinotecan, topotecan, etoposide, daunorubicin, doxorubicin, epirubicin, idarubicin, pirarubicin, mitoxantrone, chlormethin, cyclophosphamide, ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

12. A process for preparing a compound of formula (I) according to claim 1, in which R3 is $CO_2$—$(C_1$-$C_6)$alkyl or $OR^8$ with $R^8H$, comprising the following steps:

(i) McMurry coupling between a compound of the following formula (II):

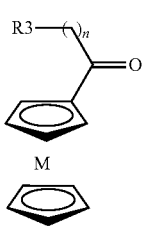

wherein M and n are as defined in claim 1 and R3 is as defined above, and a compound of the following formula (III):

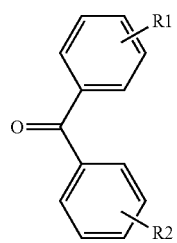

wherein R1 and R2 are as defined in claim 1, to give a compound of formula (I) as defined above, and (ii) optionally salification or solvatation of the compound of formula (I) obtained in step (i) to give a pharmaceutically acceptable salt or solvate thereof.

13. A process for preparing a compound of formula (I) according to claim 1, in which R3 is $OR^8$, comprising the following steps:

(a) reduction of a compound of the following formula (Ib):

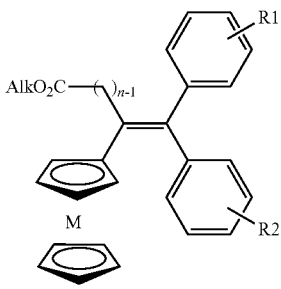

wherein M, n, R1 and R2 are as defined in claim 1 and Alk is $(C_1-C_6)$alkyl, to give a compound of formula (I) in which R3 is OH, (b) optionally substitution of the compound obtained in step (a) to give a compound of formula (I) in which R3 is $OR^8$ with $R^8H$, and (c) optionally salification or solvatation of the compound of formula (I) obtained in step (a) or (b) to give a pharmaceutically acceptable salt or solvate thereof.

14. A process for preparing a compound of formula (I) according to claim 1, in which R3 is COOH, comprising the following steps:

(1) saponification of a compound of the following formula (Ic):

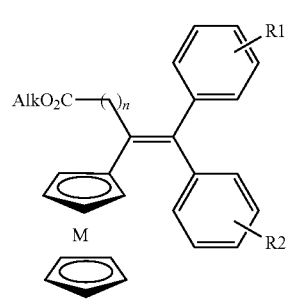

wherein M, n, R1 and R2 are as defined in claim 1 and Alk is $(C_1-C_6)$alkyl, to give a compound of formula (I) in which R3 is COOH, and (2) optionally salification or solvatation of the compound of formula (I) obtained in step (1) to give a pharmaceutically acceptable salt or solvate thereof.

15. A process for preparing a compound of formula (I) according to claim 1, in which R3 is $NR^9R^{10}$, comprising the following steps:

(A) reaction of a compound of the following formula (Id):

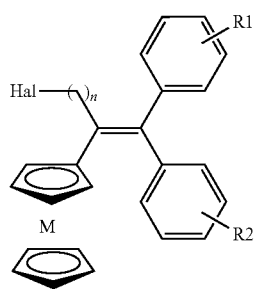

wherein M, n, R1 and R2 are as defined in claim 1 and Hal is a halogen atom,
with a compound of formula $HNR^9R^{10}$,
to give a compound of formula (I) in which R3 is $NR^9R^{10}$, and (B) optionally salification or solvatation of the compound of formula (I) obtained in step (A) to give a pharmaceutically acceptable salt or solvate thereof.

16. A method for the treatment of cancer comprising administering to a patient in need thereof an effective amount of a compound according to claim 1.

17. The method according to claim 16, wherein the compound is used alone or in combination, simultaneously, separately or sequentially, with ionizing or non-ionizing radiations or with at least one additional active ingredient.

18. The method according to claim 17, wherein the at least one additional active ingredient is selected from 6-mercaptopurin, fludarabin, cladribin, pentostatin, cytarabin, 5-fluorouracil, gemcitabin, methotrexate, raltitrexed, irinotecan, topotecan, etoposide, daunorubicin, doxorubicin, epirubicin, idarubicin, pirarubicin, mitoxantrone, chlormethin, cyclophosphamide, ifosfamide, melphalan, chlorambucil, busulfan, carmustin, fotemustin, streptozocin, carboplatin, cisplatin, oxaliplatin, procarbazin, dacarbazin, bleomycin, vinblastin, vincristin, vindesin, vinorelbin, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

* * * * *

UNITED STATES PATENT AND TRADEMARK OFFICE
CERTIFICATE OF CORRECTION

PATENT NO. : 9,758,541 B2  
APPLICATION NO. : 15/032877  
DATED : September 12, 2017  
INVENTOR(S) : Gerard Jaouen et al.

Page 1 of 1

It is certified that error appears in the above-identified patent and that said Letters Patent is hereby corrected as shown below:

In the Claims

Claim 12, Column 44, Line 67 please delete "$R^8H$" and insert --$R^8 \neq H$--

Claim 13, Column 45, Line 61 please delete "$R^8H$" and insert --$R^8 \neq H$--

Signed and Sealed this  
Tenth Day of July, 2018

Andrei Iancu  
*Director of the United States Patent and Trademark Office*